United States Patent
Fukami et al.

(10) Patent No.: US 10,669,545 B2
(45) Date of Patent: Jun. 2, 2020

(54) TUMOR CELL MALIGNANT TRANSFORMATION SUPPRESSOR AND ANTI-TUMOR AGENT

(71) Applicant: JAPAN SCIENCE AND TECHNOLOGY AGENCY, Kawaguchi-shi (JP)

(72) Inventors: Kiyoko Fukami, Tokyo (JP); Reiko Satow, Tokyo (JP)

(73) Assignee: JAPAN SCIENCE AND TECHNOLOGY AGENCY, Kawaguchi-shi (JP)

(*) Notice: Subject to any disclaimer, the term of this patent is extended or adjusted under 35 U.S.C. 154(b) by 67 days.

(21) Appl. No.: 15/569,559

(22) PCT Filed: Apr. 22, 2016

(86) PCT No.: PCT/JP2016/062757
§ 371 (c)(1),
(2) Date: Oct. 26, 2017

(87) PCT Pub. No.: WO2016/178374
PCT Pub. Date: Nov. 10, 2016

(65) Prior Publication Data
US 2019/0062751 A1    Feb. 28, 2019

(30) Foreign Application Priority Data
May 1, 2015   (JP) ................................ 2015-093980

(51) Int. Cl.
| | | |
|---|---|---|
| C12N 15/11 | (2006.01) | |
| C12N 15/113 | (2010.01) | |
| A61K 31/713 | (2006.01) | |
| A61K 48/00 | (2006.01) | |
| A61K 45/00 | (2006.01) | |
| C07K 14/47 | (2006.01) | |
| A61P 35/04 | (2006.01) | |
| C12Q 1/6886 | (2018.01) | |

(52) U.S. Cl.
CPC ........ *C12N 15/1135* (2013.01); *A61K 31/713* (2013.01); *A61K 45/00* (2013.01); *A61K 48/00* (2013.01); *A61P 35/04* (2018.01); *C07K 14/4702* (2013.01); *C12Q 1/6886* (2013.01); *C12N 2310/14* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2009/0285836 A1 | 11/2009 | Baritaki et al. |
| 2009/0317392 A1 | 12/2009 | Nakamura et al. |
| 2010/0210707 A1 | 8/2010 | Li et al. |
| 2015/0104869 A1 | 4/2015 | Li et al. |

FOREIGN PATENT DOCUMENTS

| | | |
|---|---|---|
| JP | 2009-502115 A | 1/2009 |
| JP | 2014-509515 A | 4/2014 |
| WO | WO 2006/113246 A2 | 10/2006 |
| WO | 2012/129100 A1 | 9/2012 |
| WO | 2014/062845 A1 | 4/2014 |

OTHER PUBLICATIONS

Extended European Search Report dated Nov. 29, 2018 in European Patent Application No. 16789510.1, 8 pages.
International Search Report dated Jul. 5, 2016 in PCT/JP2016/062757 filed Apr. 22, 2016.
Steinar Aamdal, "Current approaches to adjuvant therapy of melanoma", European Journal of Cancer, Sep. 2011, vol. 47, Suppl. 3, 3 total pages.
Christian U. Blank et al., "Combination of targeted therapy and immunotherapy in melanoma", Cancer Immunology Immunotherapy, Aug. 17, 2011, vol. 60, pp. 1359-1371.
Sebastien Cagnol et al., "ERK and cell death: Mechanisms of ERK-induced cell death—apoptosis, autophagy and senescence", FEBS Journal, 2009, vol. 277, pp. 2-21.
Poulikos I. Poulikakos et al., "RAF inhibitor resistance is mediated by dimerization of aberrantly spliced BRAF(V600E)", Nature, Nov. 23, 2011, vol. 480, No. 7377, 14 total pages.
Timothy J. Price et al., "Impact of KRAS and BRAF Gene Mutation Status on Outcomes From the Phase III AGITG MAX Trial of Capecitabine Alone or in Combination With Bevacizumab and Mitomycin in Advanced Colorectal Cancer", Journal of Clinical Oncology, Jul. 1, 2011, vol. 29, No. 19, pp. 2675-2682.
Jessie Villanueva et al., "Resistance to BRAF inhibitors: Unraveling mechanisms and future treatment options", Cancer Research, Dec. 1, 2011, vol. 71, No. 23, 7 total pages.

(Continued)

*Primary Examiner* — Ekaterina Poliakova-Georgantas
(74) *Attorney, Agent, or Firm* — Oblon, McClelland, Maier & Neustadt, L.L.P.

(57) ABSTRACT

The present invention provides an anti-tumor agent and a suppressor for suppressing malignant transformation such as acquisition of metastatic ability or acquisition of apoptosis resistance of a tumor cell. The present invention provides a tumor cell malignant transformation suppressor, including a substance suppressing or inhibiting Zic5 gene functions as an active ingredient to suppress or inhibit acquisition of metastatic ability or acquisition of apoptosis resistance of a tumor cell; a method of suppressing tumor cell malignant transformation of animals other than humans, including suppressing or inhibiting Zic5 gene functions to suppress or inhibit acquisition of metastatic ability or acquisition of apoptosis resistance of a tumor cell; an anti-tumor agent including a substance suppressing or inhibiting Zic5 gene functions as an active ingredient, in which the agent is used in prostate cancer therapy; and a marker for tumor cell malignancy consisting of the expression level of Zic5 gene.

12 Claims, 21 Drawing Sheets

Specification includes a Sequence Listing.

(56) References Cited

OTHER PUBLICATIONS

Jean Paul Thiery et al., "Epithelial-Mesenchymal Transitions in Development and Disease", Cell, Nov. 25, 2009, vol. 139, pp. 871-890.

Soledad R. Alonso et al., "A High-Throughput Study in Melanoma Identifies Epithelial-Mesenchymal Transition as a Major Determinant of Metastasis", Cancer Research, Apr. 1, 2007, vol. 67, No. 7, 12 total pages.

Julie Caramel et al., "A Switch in the Expression of Embryonic EMT-Inducers Drives the Development of Malignant Melanoma", Cancer Cell, Oct. 14, 2013, vol. 24, pp. 466-480.

Kristin Andersen et al., "Expression of S100A4 combined with reduced E-cadherin expression predicts patient outcome in malignant melanoma", Modern Pathology, 2004, vol. 17, pp. 990-997.

Hervé Acloque et al., "Epithelial-mesenchymal transitions: the importance of changing cell state in development and disease", The Journal of Clinical Investigation, Jun. 2009, vol. 119, No. 6, pp. 1438-1449.

Reiko Satow et al., "β-Catenin Inhibits Promyelocytic Leukemia Protein Tumor Suppressor Function in Colorectal Cancer Cells", Gastroenterology, Mar. 2012, vol. 142, No. 3, pp. 572-581.

Kaori Kanemaru et al., "Epidermal phospholipase Cδ1 regulates granulocyte counts and systemic interleukin-17 levels in mice", Nature Communications, Jul. 17, 2012, vol. 3, 12 total pages.

Imanol Arozarena et al., "Oncogenic BRAF Induces Melanoma Cell Invasion by Downregulating the cGMP-Specific Phosphodiesterase PDE5A", Cancer Cell, Jan. 18, 2011, vol. 19, pp. 45-57.

Victoria Sanz-Moreno et al., "ROCK and JAK1 Signaling Cooperate to Control Actomyosin Contractility in Tumor Cells and Stroma", Cancer Cell, Aug. 16, 2011, vol. 20, pp. 229-245.

Tamaki Hirano et al., "Identification of novel small compounds that restore E-cadherin expression and inhibit tumor cell motility and invasiveness", Biochemical Pharmacology, 2013, vol. 86, No. 10, pp. 1419-1429.

Akira Ishiguro et al., "Molecular properties of Zic4 and Zic5 proteins: functional diversity within Zic family", Biochemical and Biophysical Research Communications, 2004, vol. 324, pp. 302-307.

Glynn Dennis Jr et al., "DAVID: Database for Annotation, Visualization, and Integrated Discovery", Genome Biology, 2003, vol. 4, No. 5, p. P3.

Angela R. Hess et al., "Focal Adhesion Kinase Promotes the Aggressive Melanoma Phenotype", Cancer Research, Nov. 1, 2005, vol. 65, No. 21, 11 total pages.

Jun Aruga et al., "Expression of ZIC family genes in meningiomas and other brain tumors", BMC Cancer, 2010, vol. 10, No. 79, pp. 1-10.

Zen Kouchi et al., "Involvement of PIP kinase IIbeta in VitaminD receptor dependent E-cadherin up-regulation in colon cancer cells", Journal of Japanese Biochemical Society Shoroku CD, 2009, 2 total pages.

*FIG. 15*
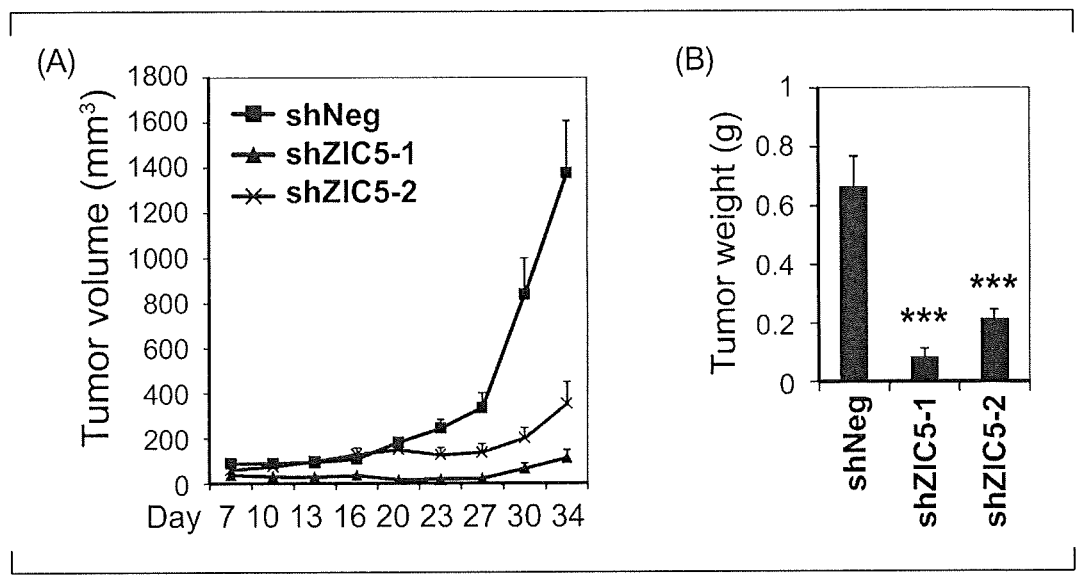
*FIG. 16*
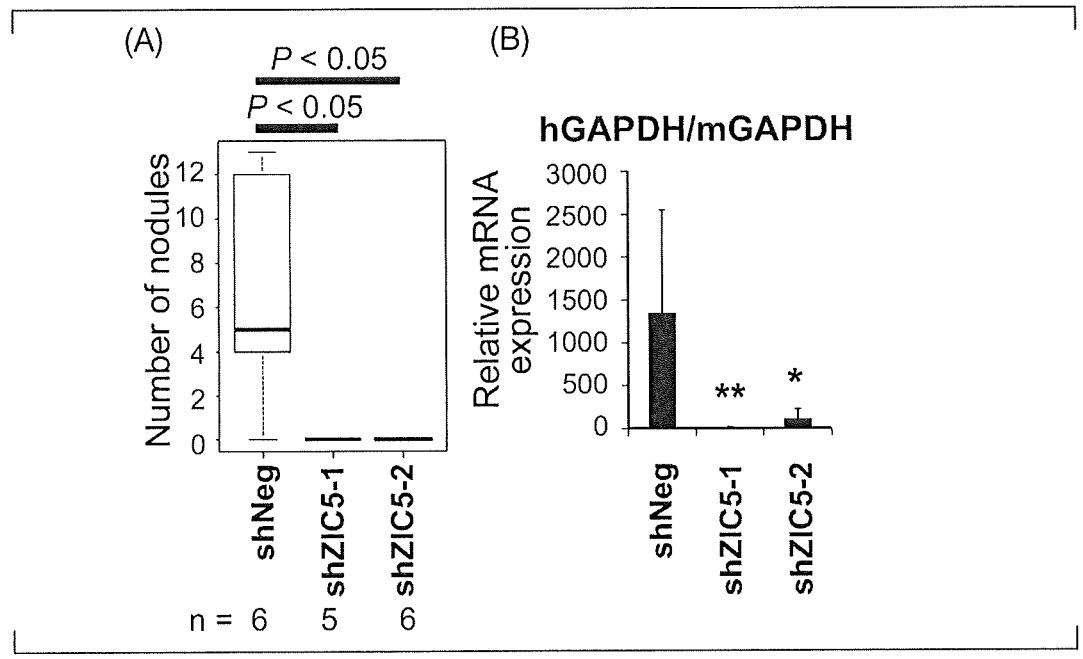
*FIG. 17*
```
GBS;    GATCCTGTGATTTTCGTCTTGGGTGGTCTCCCTCG (SEQ ID NO: 15)
M5;     GATCCTGTGATTTTCGTCTTGGGTGATCTCCCTCG (SEQ ID NO: 16)
pCDH1;  TCAGCCAATCAGCGGTACGGGGGGCGGTGCCTCCG  (SEQ ID NO: 17)
```

TUMOR CELL MALIGNANT TRANSFORMATION SUPPRESSOR AND ANTI-TUMOR AGENT

TECHNICAL FIELD

The present invention relates to an anti-tumor agent and a suppressor for suppressing malignant transformation such as acquisition of metastatic ability or acquisition of apoptosis resistance of a tumor cell.

Priority is claimed on Japanese Patent Application No. 2015-93980, filed on May 1, 2015, the content of which is incorporated herein by reference.

BACKGROUND ART

Malignant melanoma (melanoma) is a malignant tumor in which melanocytes, which are melanin-producing cells, become cancerous. It is curable by early detection, but the five-year survival rate in a case where distant metastasis has occurred is as low as about 10% and an effective therapy has not yet been established (for example, refer to NPLs 1 and 2). A BRAF$^{V600E}$ gene mutation has been confirmed in about 60% to 70% or more of cases. By BRAF (MAPKKK of MAPK pathway), downstream MEK (MAPKK of MAPK pathway) is phosphorylated and activated, and by the activated MEK, further downstream ERK (MAPK of MAPK pathway) is phosphorylated and activated, and therefore, many proteins associated with proliferation, survival, invasion, and metastasis are activated (for example, refer to NPL 3). BRAF being constantly and strongly activated by BRAF$^{V600E}$ mutation is one of the causes of melanoma. Clinical trials using a selective inhibitor (PLX4032, vemurafenib) of mutant BRAF are being conducted currently, and a high response rate has been confirmed. It has been reported that the effect of BRAF inhibitors becomes limited, as drug resistance against it occurs due to various mechanisms such as expression of splicing variants of the BRAF gene and expression of hepatocyte growth factor (HGF) secreted by interstitial cells (for example, refer to NPLs 4 to 6).

Epithelial Mesenchymal Transition (EMT) is known as one of the causes of epithelial cancer acquiring metastatic ability. EMT is a phenomenon in which epithelial cells acquire the trait of mesenchymal cells, and it is known that when EMT occurs, the expression level of E-cadherin, which is an epithelial cell adhesion molecule, is decreased. In addition, it has been revealed that EMT is regulated by a transcription factor such as Snail, Slug, and Twist, and it is known that these factors regulate expression of E-cadherin and the like, by which EMT is induced (for example, refer to NPL 7).

In melanoma, many expressions of EMT-implicated genes are altered in a case where metastasis has occurred, and it has been suggested that an enhanced EMT program is one of the causes of metastasis (for example, refer to NPL 8). In addition, in melanoma having a BRAF mutation, expression of transcription factors such as Zeb 1 and Twist 1 are induced by constitutive activation of BRAF, inhibition of E-cadherin expression by these factors, and EMT-like phenomenon that melanoma exacerbation is caused Have been confirmed. (for example, refer to NPL 9). It has been reported that the expression level of E-cadherin decreased in many melanomas, and the recurrence rate significantly increased in cases where the expression of E-cadherin is decreased (for example, refer to NPL 10). These findings suggest an association between decreased expression of E-cadherin and enhanced malignancy of melanoma.

EMT is an essential phenomenon not only in cancer but also during early embryonic development, and is involved in gastrulation and neural crest cell differentiation. Neural crest cells induce EMT in a part of the dorsal neural tube, separated from the epithelial tissue, and therefore acquire migration ability, and then differentiate into cells of the peripheral nervous system, glial cells, satellite cells, melanocytes, odontoblasts, craniofacial cartilage, and the like. Also by EMT of neural crest cells, decreased expression of E-cadherin is induced by transcription factors such as Snail, Slug, and Twist (for example, refer to NPLs 7 and 11).

CITATION LIST

Non-Patent Literature

[NPL 1] Aamdal et al., European Journal of Cancer, 2011, vol. 47, Suppl 3, p. S336-S337.
[NPL 2] Blank et al., Cancer Immunology, Immunotherapy, 2011, vol. 60, p. 1359-1371.
[NPL 3] Cangol et al., FEBS Journal, 2009, vol. 277(1), p. 2-27.
[NPL 4] Poulikakos et al., Nature, 2011, vol. 480, p. 387-390.
[NPL 5] Price et al., Journal of Clinical Oncology 2011, vol. 29(19), p. 2675-2682.
[NPL 6] Villanueva et al., Cancer Research, 2011, vol. 71, p. 7137.
[NPL 7] Thiery et al., Cell, 2009, vol. 139, p. 871-890.
[NPL 8] Alonso et al., Cancer Research, 2007, vol. 67(7), p. 3450-3460.
[NPL 9] Caramel et al., Cancer Cell, 2013, vol. 24, p. 466-480.
[NPL 10] Andersen et al., Modern Pathology, 2004, vol. 17, p. 990-997.
[NPL 11] Acloque et al., Journal of Clinical Investigation, 2009, vol. 119, p. 1438-1449.
[NPL 12] Satow et al., Gastroenterology, 2012, vol. 142(3), p. 572-581.
[NPL 13] Kanemaru et al., Nature Communications, 2012, vol. 3, p. 963.
[NPL 14] Arozarena et al., Cancer Cell, 2011, vol. 19, p. 45-57.
[NPL 15] Sanz-Moreno et al., Cancer Cell, 2011, vol. 20, p. 229-245.
[NPL 16] Hirano et al., Biochemical Pharmacology, 2013, vol. 86(10), p. 1419-1429.
[NPL 17] Ishigro Ishiguro et al., Biochemical and Biophysical Research Communications, 2004, vol. 324, p. 302-307.
[NPL 18] Dennis et al., Genome Biology, 2003, vol. 4(5), p. P3.
[NPL 19] Hess et al., Cancer Research, 2005, vol. 65, p. 9851-9860.

SUMMARY OF INVENTION

Technical Problem

An object of the present invention is to provide an anti-tumor agent and a suppressor for suppressing malignant transformation such as acquisition of metastatic ability or acquisition of apoptosis resistance of a tumor cell.

Solution to Problem

As a result of intensive research, the inventors of the present invention have found that by suppressing Zic5 (Zic family member 5 (odd-paired homolog, Drosophila)) gene expression in tumor cells, a reduction in the expression level of E-cadherin is suppressed and Zic5 protein functions as a transcription factor of E-cadherin, and therefore have completed the present invention.

A tumor cell malignant transformation suppressor, a method of suppressing tumor cell malignant transformation, an anti-tumor agent, a marker for tumor cell malignancy, a method of evaluating tumor cell malignancy, and a tumor marker are described in [1] to [15] as below.

[1] A tumor cell malignant transformation suppressor, including a substance suppressing or inhibiting Zic5 gene functions as an active ingredient to suppress or inhibit acquisition of metastatic ability or acquisition of apoptosis resistance of a tumor cell.

[2] The tumor cell malignant transformation suppressor according to [1], in which the substance suppressing or inhibiting Zic5 gene functions is siRNA targeting Zic5 gene.

[3] The tumor cell malignant transformation suppressor according to [1], in which the substance suppressing or inhibiting Zic5 gene functions is a substance inhibiting interaction between Zic5 protein and a promoter sequence of a gene that codes for E-cadherin, a substance inhibiting Zic5 protein subnuclear localization, or a substance degrading Zic5 protein.

[4] The tumor cell malignant transformation suppressor according to any one of [1] to [3], in which the tumor cell is a melanoma cell or a prostate cancer cell.

[5] The tumor cell malignant transformation suppressor according to any one of [1] to [4], in which the tumor cell is resistant to a BRAF inhibitor.

[6] A method of suppressing tumor cell malignant transformation of animals other than humans, including suppressing or inhibiting Zic5 gene functions to suppress or inhibit acquisition of metastatic ability or acquisition of apoptosis resistance of a tumor cell.

[7] The method of suppressing tumor cell malignant transformation according to [6], in which suppressing or inhibiting Zic5 gene functions is carried out by inhibiting expression of Zic5 gene by RNA interference.

[8] An anti-tumor agent including a substance suppressing or inhibiting Zic5 gene functions as an active ingredient, in which the agent is used in melanoma therapy.

[9] The anti-tumor agent according to [8], in which the agent is used in therapy of melanoma which is resistant to a BRAF inhibitor, or melanoma which has no sensitivity to BRAF inhibitor treatment.

[10] An anti-tumor agent including a substance suppressing or inhibiting Zic5 gene functions as an active ingredient, in which the agent is used in prostate cancer therapy.

[11] The anti-tumor agent according to any one of [8] to [10], in which the substance suppressing or inhibiting Zic5 gene functions is siRNA targeting Zic5 gene.

[12] A marker for tumor cell malignancy consisting of the expression level of Zic5 gene.

[13] A method of evaluating tumor cell malignancy, including evaluating the malignancy to become higher as the expression level of Zic5 gene in a test tumor cell becomes higher, using the expression level of Zic5 gene in the test tumor cell as a marker.

[14] The method of evaluating tumor cell malignancy according to [13], in which in a case where the test tumor cell is a primary tumor cell and the expression level of Zic5 gene in the test tumor cell is a predetermined threshold or more, a risk that the test tumor cell has acquired metastatic ability or apoptosis resistance is evaluated to be high.

[15] A tumor marker consisting of the expression level of Zic5 gene and detecting melanoma or prostate cancer.

Advantageous Effects of Invention

A tumor cell malignant transformation suppressor and an anti-tumor agent related to the present invention suppress a reduction in the expression level of E-cadherin in tumor cells, and thus can suppress malignant transformation such as acquisition of metastatic ability or acquisition of apoptosis resistance. The tumor cell malignant transformation suppressor and the like related to the present invention have an effect of suppressing malignant transformation and an anti-tumor effect even with respect to tumor cells which have $BRAF^{V600E}$ mutation and tumor cells which acquired a drug resistance to a BRAF inhibitor, vemurafenib, and thus are extremely effective novel drugs in tumor therapy.

The expression level of Zic5 gene in tumor cells is useful as a marker for tumor cell malignancy, and therefore, a method of evaluating tumor cell malignancy related to the present invention is useful for early detection of metastatic tumor and evaluation of a risk of drug resistance acquisition.

BRIEF DESCRIPTION OF DRAWINGS

FIG. 15 illustrates changes over time in volume (A) and weight (B) of a tumor of nude mice into which each cell was subcutaneously transplanted in Example 4.

FIG. 16 illustrates measurement results of lung metastatic ability in nude mice into which shNeg line, shZic5-1 line, or shZic5-2 line is inoculated in Example 4.

FIG. 17 is an alignment view of base sequences of three probes used in EMSA of Example 5.

DESCRIPTION OF EMBODIMENTS

Figure 1:
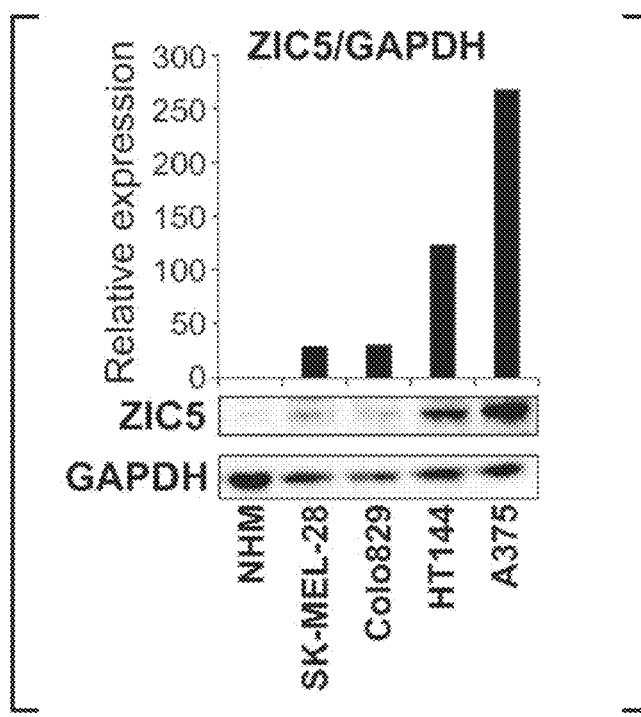
FIG. 1 illustrates results of quantifying the expression level of Zic5 gene with GAPDH gene as an internal control of each cell in Example 1.

In the present invention and the specification of the present application, "tumor cell malignant transformation" means a phenomenon in which a tumor cell acquires metastatic ability or acquires drug resistance such as apoptosis resistance.

A tumor cell malignant transformation suppressor according to the present invention is characterized to include a substance suppressing or inhibiting Zic5 gene functions as an active ingredient to suppress or inhibit acquisition of metastatic ability or acquisition of apoptosis resistance of a tumor cell. Zic5 protein coded by Zic5 gene binds to a sequence GGGCGGT in a promoter region of a gene (CDH1 gene) that codes for E-cadherin, by which E-cadherin expression is regulated. The higher the expression level of Zic5 gene becomes, the more the E-cadherin expression is suppressed, by which EMT occurs, and therefore metastatic ability and apoptosis resistance are easily acquired. Conversely, a reduction of the expression level of E-cadherin is suppressed by suppressing Zic5 gene expression, and therefore EMT becomes unlikely to occur. Accordingly, transfection of a tumor cell with the tumor cell malignant transformation suppressor according to the present invention enables EMT suppression and malignant transformation suppression. Zic5 protein functioning as a transcription factor of CDH1 gene is knowledge found for the first time by the inventors of the present application. There is a possibility that Zic5 protein functions as a transcription factor of a gene that codes for a protein other than E-cadherin, and tumor cell malignant transformation is likely to be suppressed by regulating expression of this protein.

Suppressing or inhibiting Zic5 gene functions can be achieved by inhibiting Zic5 gene expression. As a substance suppressing or inhibiting Zic5 gene functions which is an active ingredient of the tumor cell malignant transformation suppressor according to the present invention, there is a substance having an effect of suppressing the expression itself of Zic5 gene due to RNA interference and the like. Examples of such a substance include siRNA (small interfering RNA), shRNA (short hairpin RNA), or miRNA (micro RNA) which have a double-stranded structure consisting of a sense strand and an antisense strand of a partial region of cDNA (target region of RNAi (RNA interference)) of Zic5 gene. The substance may be a RNAi-inducing vector by which siRNA and the like can be produced in a target tumor cell. Regarding production of siRNA, shRNA, miRNA, and RNAi-inducing vectors, it is possible to design and manufacture the vectors by a usual method from base sequence information of cDNA of target Zic5 gene. The RNAi-inducing vector can be produced by inserting a base sequence of aRNAi target region to a base sequence of various commercially available RNAi vectors.

An active ingredient of the tumor cell malignant transformation suppressor according to the present invention may be a substance that binds to Zic5 protein directly or indirectly, and suppresses or inhibits the binding of the Zic5 protein to a promoter sequence of CDH1 gene. The substance is not particularly limited and may be any one of a nucleic acid, a peptide, a protein, and a low-molecular-weight compound.

Examples of the nucleic acid that binds to Zic5 protein to inhibit interaction between Zic5 protein and a promoter sequence of CDH1 gene include a nucleic acid molecule having a base sequence which is identical to or highly homologous to a binding region with Zic5 protein in a promoter sequence of CDH1 gene (GGGCGGT). The nucleic acid molecule is so called decoy nucleic acid molecule. The decoy nucleic acid molecule may be DNA or RNA, or may be a single-stranded nucleic acid or a double-stranded nucleic acid. It is preferable that the decoy nucleic acid molecule be a double-stranded DNA because of its excellent stability in a living body.

Examples of the protein that binds to Zic5 protein to inhibit interaction between Zic5 protein and a promoter sequence of CDH1 gene include an anti-ZIC5 antibody. The antibody may be a monoclonal antibody or a polyclonal antibody. The antibody may be an artificially synthesized antibody such as a chimeric antibody, a single chain antibody, and a humanized antibody. These antibodies can be manufactured by a usual method.

The active ingredient of the tumor cell malignant transformation suppressor according to the present invention may be a substance inhibiting subnuclear localization of Zic5 protein. If subnuclear localization of Zic5 protein is inhibited, Zic5 protein cannot bind to a promoter sequence of CDH1 gene, and therefore a function as a transcription factor of CDH1 gene is inhibited. A substance inhibiting subnuclear localization of Zic5 protein may be a substance inhibiting the translocation of Zic5 protein into the nucleus and may be a substance promoting the exportation to the outside of the nucleus. Examples of the substance inhibiting the translocation into the nucleus include a substance that binds to Zic5 protein so as to cover the nuclear localization signal of Zic5 protein. The substance may be a protein or a peptide, or may be a low-molecular-weight compound.

The active ingredient of the tumor cell malignant transformation suppressor according to the present invention may be a substance degrading Zic5 protein. The degradation of Zic5 protein itself inhibits a function thereof. A substance degrading Zic5 protein may be a proteolytic enzyme which directly degrades Zic5 protein, or may be a substance that carry out various kinds of labeling such as polyubiquitin for Zic5 protein so as to become a substrate for a proteolytic enzyme.

The tumor cell malignant transformation suppressor according to the present invention can be formulated into a dosage form suitable for various administration forms such as oral administration, intravenous injection, direct administration through the nasal cavity or oral cavity, and transdermal administration, according to a usual method. Examples of the dosage form include tablets, powders, granules, capsules, chewable tablets, syrups, solutions, suspensions, injections, oral rinses, sprays, patches, ointments, and the like.

The tumor cell malignant transformation suppressor according to the present invention may contain various kinds of additives in addition to the substance suppressing or inhibiting Zic5 gene functions as an active ingredient. Examples of such additives include excipients, binders, lubricants, wetting agents, solvents, disintegrants, solubilizing agents, suspending agents, emulsifying agents, tonicity agents, stabilizing agents, buffering agents, preservatives, antioxidants, flavoring agents, coloring agents, and the like. These additives are pharmaceutically acceptable substances, and can be appropriately selected from those used for pharmaceutical formulation so as to be used.

By administering the tumor cell malignant transformation suppressor according to the present invention to humans or animals other than humans to suppress or inhibit Zic5 gene functions, tumor cells in these animals are suppressed or inhibited from acquiring metastatic ability or apoptosis resistance, and malignantization of these tumor cells can be suppressed. The animals are not particularly limited, and may be humans or animals other than humans. Examples of the non-human animals include mammals such as cattle, swine, horse, sheep, goat, monkey, dog, cat, rabbit, mouse, rat, hamster, and guinea pig, and birds such as chicken, quail, and duck.

The tumor cell malignant transformation suppressor according to the present invention can suppress malignant transformation of various tumor cells. A target tumor cell may be a tumor cell derived from metastatic cancer, but is preferably a tumor cell derived from primary cancer because an effect of suppressing malignant transformation is sufficiently represented.

The type of the tumor cell targeted by the tumor cell malignant transformation suppressor according to the present invention is not particularly limited, and examples thereof include cells of skin cancer, prostate cancer, thyroid cancer, lung cancer, breast cancer, liver cancer, pancreas cancer, bile duct cancer, adrenal cancer, stomach cancer, colorectal cancer, kidney cancer, cervical cancer, uterine body cancer, ovarian cancer, bladder cancer, liposarcoma, fibrosarcoma, leiomyosarcoma, rhabdomyosarcoma, synovial sarcoma, malignant peripheral nerve sheath tumor, osteosarcoma, chondrosarcoma, leukemia, lymphoma, myeloma, and the like. As the tumor cell for which the tumor cell malignant transformation suppressor according to the present invention is used as a therapeutic agent, tumor cells derived from epithelial cells in which the expression level of E-cadherin is originally high are preferable, skin cancer cells or prostate cancer cells are preferable because the expression level of Zic5 gene is high, and melanoma cells or prostate cancer cells are more preferable. Particularly, the tumor cell malignant transformation suppressor according to the present invention exhibits the effect of suppressing malignant transformation even with respect to tumor cells which are resistant to a BRAF inhibitor such as vemurafenib, or tumor cells which have no sensitivity to BRAF inhibitor treatment (that is, which has no $BRAF^{V600E}$ mutation), and therefore is suitably used in therapy of a tumor having these tumor cells.

In skin cancer such as melanoma or prostate cancer, suppressing or inhibiting Zic5 gene functions can suppress not only malignant transformation but also proliferation of tumor cells. Accordingly, the substance suppressing or inhibiting Zic5 gene functions can also be used as an active ingredient of an anti-tumor agent used in therapy of skin cancer such as melanoma or prostate cancer. As the substance suppressing or inhibiting Zic5 gene functions, it is possible to use the same substance as the active ingredient of the tumor cell malignant transformation suppressor according to the present invention. Particularly, an anti-tumor agent according to the present invention is an extremely effective therapeutic agent with respect to melanoma which is resistant to the BRAF inhibitor and for which there was no effective therapeutic agent, or melanoma which has no sensitivity to BRAF inhibitor treatment of the related art.

As the expression level of Zic5 gene becomes high in tumor cells, the E-cadherin expression is suppressed more, by which EMT occurs, and therefore malignant transformation is likely to occur. Conversely, in tumor cells in which the expression level of Zic5 gene became lower, the E-cadherin expression level does not decrease, by which EMT becomes unlikely to occur, and therefore malignant transformation is unlikely to occur. Therefore, the expression level of Zic5 gene in tumor cells is useful as a malignancy marker. By using the expression level of Zic5 gene in test tumor cells as a marker, it is possible to evaluate malignancy in the test tumor cells based on the expression level of Zic5 gene.

For example, it can be evaluated that the higher the expression level of Zic5 gene in the test tumor cells becomes, the higher the malignancy is. Conversely, it can be evaluated that the lower the expression level of Zic5 gene in the test tumor cells becomes, the lower the malignancy is. The expression level of Zic5 gene in the test tumor cells is compared to a predetermined threshold, and then malignancy of the test tumor cells may be evaluated. In a case where the expression level of Zic5 gene is higher than the predetermined threshold, malignancy of the test tumor cells is evaluated to be high, and in a case where the expression level is lower than the predetermined threshold, malignancy of the test tumor cells is evaluated to be low. For example, in a case where the test tumor cells are primary tumor cells and the expression level of Zic5 gene in these test tumor cells is equal to or higher than the predetermined threshold, it is possible to evaluate that a risk that the test tumor cells has acquired metastatic ability or apoptosis resistance is high.

The threshold can be appropriately set by considering types and the like of a method of measuring the expression level of Zic5 gene, or by performing a required preliminary test and the like. For example, a measurement value of the expression level of Zic5 gene in cells of non-malignant group, which contains tumor cells confirmed not to be malignantly transformed from a result of other test methods and a cell group of non-tumor cells, is compared to a measurement value of the expression level of Zic5 gene in cells of non-malignant group, which is a cell group of tumor cells in which acquisition of metastatic ability or apoptosis resistance is confirmed, and therefore the threshold for identifying the both groups can be appropriately set.

The expression level of Zic5 gene of the test tumor cells may be measured by an mRNA level, or may be measured by a protein level. The method of measuring the expression level of Zic5 gene is not particularly limited as long as it is a method capable of quantitatively or semi-quantitatively measuring a level of a target protein or a level of a target mRNA in the cells, and can be appropriately selected from a known method used for detecting mRNA or protein in a specimen, and then used. Each method can be performed through a usual method.

An mRNA level of Zic5 gene may be detected by a hybridization method using a probe capable of hybridizing to mRNA of Zic5 gene, or may be detected by a method using a nucleic acid amplification reaction in which a primer capable of hybridizing to mRNA of Zic5 gene and a polymerase are used. Commercially available detection kits and the like can be used. For example, after synthesizing cDNA by performing a reverse transcription reaction using total RNA extracted from test tumor cells as a template, PCR (Polymerase Chain Reaction) and the like are performed using the obtained cDNA as a template, and then an amount of amplified product obtained is measured, and therefore an mRNA level of Zic5 gene can be quantified. The amplified product can be quantitatively measured by specific separation by gel or capillary electrophoresis and then detection. Furthermore, at the same time of detecting mRNA of Zic5 gene, quantitation thereof can be easily performed by performing semi-quantitative PCR such as real-time PCR instead of PCR.

A level of Zic5 protein can be measured by using an antibody (anti-ZIC5 antibody) that binds specifically to Zic5 protein. For example, immunostaining is performed using anti-ZIC5 antibody as a primary antibody, and the presence or absence of Zic5 expression in test tumor cells and expression intensity are checked based on the presence or absence of stained substance and staining intensity. The immunostaining may be an enzyme antibody staining method using an enzyme-labeled antibody or may be a fluorescent antibody staining method using a fluorescently labeled antibody. After separating proteins in a cell extract prepared from the test tumor cells by SDS-PAGE and the like, a level of Zic5 protein in test tumor cells can be quantitatively measured by western blotting and the like.

The expression level of Zic5 gene in melanoma cells or prostate cancer cells is higher compared to cells before becoming cancerous. Accordingly, the expression level of Zic5 gene is useful as a tumor marker which is characterized to detect melanoma or prostate cancer. For example, in a case where the expression level of Zic5 gene is higher than a predetermined threshold, test cells are evaluated to be melanoma cells or prostate cancer cells, and in a case where the expression level is lower than a predetermined threshold, test cells are evaluated to be cells that did not become cancerous. For example, a measurement value of the expression level of Zic5 gene in cells of normal cell group, which is a cell group of cells confirmed not to become cancerous from a result of other test methods, is compared to a measurement value of the expression level of Zic5 gene in cells of melanoma cell group, which is a cell group of cells confirmed to be melanoma cells, and therefore the threshold for identifying the both groups can be appropriately set.

EXAMPLES

Next, the present invention will be described in more detail by showing examples and the like, but the present invention is not limited to the following examples. Animal experiments were performed at the Tokyo University of Pharmacy and Life Sciences in compliance with the Guidelines for Laboratory Animal Research under the approval of the institutional ethics committee.
<Cell Culture>
Cells used in the following example were cultured as follows.

Four types of cell lines (SK-MEL-28 cells, Colo 829 cells, HT 144 cells, and A375 cells), which are melanoma cell lines, and DU145 cells, which are a prostate cancer cell line, were obtained from ATCC (American Type Culture Collection) to be used. PC3 cells, which are prostate cancer cell lines, were obtained from JCRB Cell Bank (National Institutes of Biomedical Innovation, Health and Nutrition). As HEK293 cells and HeLa cells, those described in NPL 12 were used. These cells were cultured in RPMI 1640 medium (manufactured by Invitrogen Corporation) containing 10% fetal bovine serum in the presence of 5% $CO_2$ at 37° C.

Example 1

Focusing on the commonality of EMT, which plays an important role in malignant transformation of cancer cells and individual generation, a human siRNA library for a gene group involved in neural crest development was produced, and using an RNA interference method, genes having an effect of suppressing E-cadherin expression in a melanoma cell line having $BRAF^{V600E}$ mutation were searched.
<Measurement of Influence on Expression Level of E-cadherin by of RNA Interference>
First, 26 genes which are essential for neural crest cell formation and differentiation and whose precise molecular mechanisms in cancer cells have not been fully elucidated were selected, and each gene was subjected to RNA interference to examine the influence on the expression level of E-cadherin. Specifically, with respect to each gene, E-cadherin in cells transfected with two types of siRNA (manufactured by QIAGEN) was detected by immunocytochemistry, and the expression level thereof was quantified. As a result, six genes of Zic5, BMPER, TES, SULF1, SULF2, and SOXIO among 26 genes affected E-cadherin expression levels. In both SK-MEL-28 cells and Colo829 cells, the expression level of E-cadherin in cells in which expression of each gene was suppressed by siRNA transfection was increased 1.5-fold or more as compared with the cells into which negative control siRNA was transfected.
<Confirmation of Zic5 Gene Expression by Western Blotting>
To confirm the expression level of Zic5 gene in melanoma and melanocytes by using a protein level, the expression level of Zic5 gene in A375 cells, HT144 cells, COL0829 cells, and SK-MEL-28 cells, which are melanoma cell lines, and normal human melanocytes (NHM) was examined by western blotting. GAPDH (glyceraldehyde-3-phosphate dehydrogenase) was used as an internal control. Western blotting was performed according to a method of Kanemaru et al. (refer to NPL 13) using anti-ZIC5 antibody (manufactured by Aviva systems biology) and anti-GAPDII antibody (manufactured by Cell Signaling).

Figure 2:
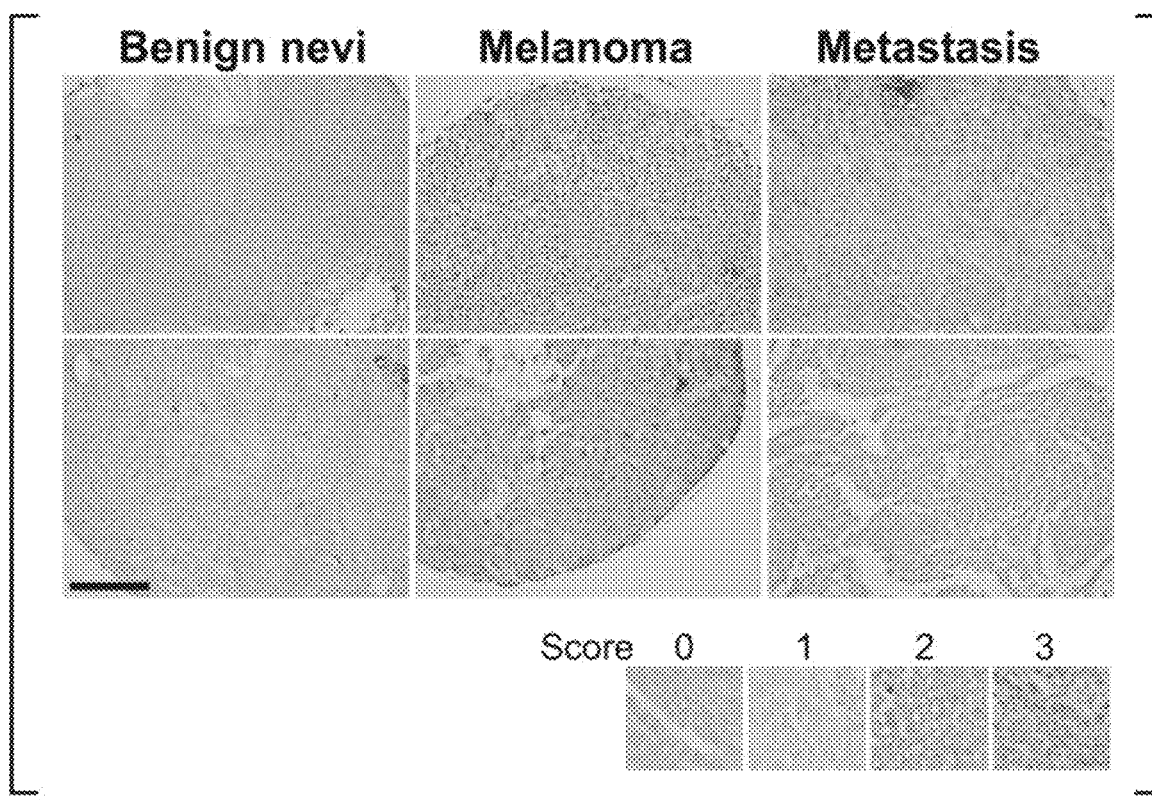
FIG. 2 illustrates stained images of a human melanoma clinical specimen subjected to immunohistochemical staining using anti-ZIC5 antibody of Example 1.

Quantitative results of the expression level of Zic5 protein with GAPDH as an internal control of each cell is shown in FIG. 1. In FIG. 1, the bottom is the result of western blotting with each cell, and the top is the expression level (relative value) of Zic5 protein calculated based on staining intensity of each band detected by western blotting. As a result, it was confirmed that the expression level of Zic5 gene was higher in all melanoma cell lines compared to the normal human melanocytes.
<ZIC5 Staining of Human Melanoma Tissue Section>
Immunohistochemical staining was performed with respect to tissue microarray (purchased from US Biomax) which contains 18 tissue sections of Benign nevus, 56 tissue sections of a cancer tissue site (melanoma), and 26 tissue sections of a metastatic site (Metastasis), which are patient tissue sections of human melanoma using anti-ZIC5 antibody (manufactured by Aviva systems biology), and Zic5 protein expression in a human melanoma clinical specimen was examined. Immunostained images are shown at the top of FIG. 2. As a result, it was found that in the cancer tissue site and the metastatic site, the expression level of Zic5 gene was greatly upregulated compared to the benign nevus.

Figure 3:
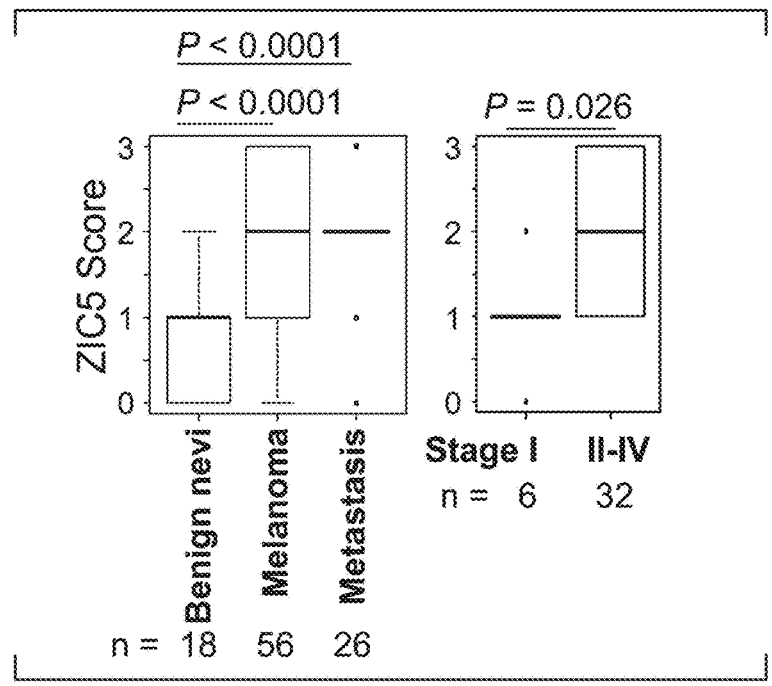
FIG. 3 illustrates results of scoring the expression level of Zic5 gene based on staining intensity of the stained images of FIG. 2 in Example 1.

The stained images of each tissue section were scored based on staining intensity into 4 stages (0 to 3). The staining intensities of each score are shown at the bottom of FIG. 2 and results of each score are shown in FIG. 3. The left of FIG. 3 shows scores of the Zic5 expression level of the stained images of the benign nevus, the cancer tissue site, and the metastatic site, and the right of FIG. 3 shows scores of the Zic5 expression level in each stage. As a result, a tendency for the expression of Zic5 gene to become higher as the stage of melanoma proceeds was shown.

Based on these results, a possibility was suggested that a candidate gene, ZIC5, which was obtained by screening, contributes to melanoma proceedings by regulating E-cadherin expression.

Example 2

To elucidate the roles of Zic5 gene in melanoma cells, a stably Zic5 gene-overexpressed line was produced using SK-MEL-28 cells, the melanoma cell line, and metastasis-related genes were examined.
<Preparation of Stably Zic5 Gene-Expressed Line>

First, the ORF of human Zic5 gene cDNA was amplified by PCR and the amplified product obtained was subcloned into the pFlag-CMV-4 expression plasmid vector (manufactured by Sigma), and an expression vector (Flag-ZIC5 expression vector) for expressing Flag-labeled ZIC5 (Flag-ZIC5) was prepared. The obtained Flag-ZIC5 expression vector was transfected into SK-MEL-28 cells using a lipofectamine reagent, "Lipofectamine 2000" (manufactured by Invitrogen Corporation) according to the product protocols. The transfected cells were seeded thinly and cultured in a medium containing 800 µg/mL of G418 (manufactured by Invitrogen Corporation) for 10 days, and therefore the stably Zic5 gene-expressed line was selected.

As a control, transfection and 6418 selection were performed in the same manner to obtain a stably Flag-expressed line, except that an empty vector (pFlag-CMV-4) by which only Flag peptide is expressed was used instead of the Flag-ZIC5 expression vector.

When the cell form of the stably Zic5 gene-expressed line and the stably Flag-expressed line (control cells) was examined by microscopy, it was observed that the number of dendrites was reduced in the stably Zic5 gene-expressed line compared to the control cells (not shown).
<Measurement of E-Cadherin Expression Level by Western Blotting>

A level of protein in E-cadherin of the stably Zic5 gene-expressed line and the stably Flag-expressed line was measured by western blotting using GAPDH as an internal control. Western blotting was performed according to a method of Kanemaru et al. (refer to NPL 13) using anti-Flag antibody (manufactured by Sigma), anti-E-cadherin antibody (manufactured by BD Biosciences), and anti-GAPDH antibody (manufactured by Cell Signaling). The measurement was performed through two independent experiments.

Figure 4:
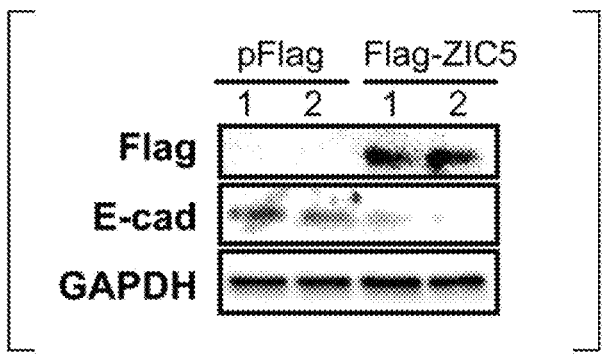
FIG. 4 illustrates western blotting images of a stably Zic5 gene-expressed line and a stably Flag-expressed line of Example 2.

Bands stained from each antibody are shown in FIG. 4. The top ("Flag") is a band stained by anti-Flag antibody, the middle ("E-cad") is a band stained by anti-E-cadherin antibody, and the bottom ("GAPDH") a band stained by anti-GAPDH antibody. In the stably Zic5 gene-expressed line in which Flag-ZIC5 is expressed ("Flag-ZIC5" in the drawing), E-cadherin expression was significantly suppressed compared to the control cells ("pFlag" in the drawing).
<Measurement of E-Cadherin Level by qRT-PCR>

An mRNA level of CDH1 gene (gene that codes for E-cadherin) of the stably Zic5 gene-expressed line and the stably Flag-expressed line was measured by qRT-PCR. An mRNA level of GAPDH gene was used as an internal control. The measurement was performed through two independent experiments.

First, total RNA of each cell was recovered and by using this as a template, and a reverse transcription reaction was performed to synthesize cDNA. For recovering of total RNA, a commercially available kit, "ReliaPrep RNA Cell Miniprep System" (manufactured by Promega, Madison, Wis.) was used, and for the reverse transcription reaction, a commercially available kit, "High Capacity cDNA Reverse Transcription kit" (manufactured by Applied Biosystems) was used, and these were performed according to the product protocols.

Next, real-time PCR was performed using the obtained cDNA as a template. Real-time PCR was performed by using a commercially available kit "THUNDERBIRD SYBR qPCR Mix" (manufactured by Toyobo, Osaka, Japan) and "CFX96" thermocycler (manufactured by Bio-Rad, Munich, Germany). Primers used are shown in Table 1.

TABLE 1

| Primer | Base Sequence | SEQ. NO. |
|---|---|---|
| CDH1 (E-cadherin) forward | GGACTTTGGCGTGGGCCAGG | 1 |
| CDH1 (E-cadherin) reverse | CCCTGTCCAGCTCAGCCCGA | 2 |
| GAPDH forward | AGCCTCCCGCTTCGCTCTCT | 3 |
| GAPDH reverse | CCAGGCGCCCAATACGACCA | 4 |

Figure 5:
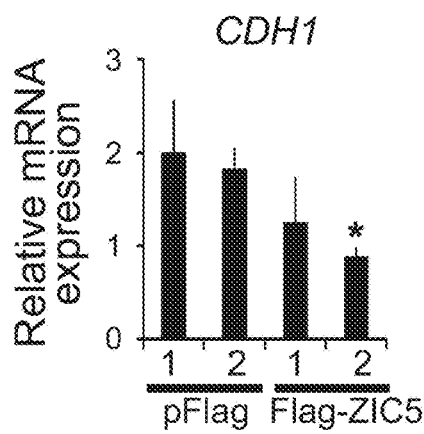
FIG. 5 illustrates measurement results of a relative mRNA expression level of CDH1 gene (gene that codes for E-cadherin) with GAPDH gene as an internal control of the stably Zic5 gene-expressed line and the stably Flag-expressed line in Example 2.

An mRNA level of CDH1 gene of each cell was normalized to an mRNA level of GAPDH gene. An average value (n=3) of a relative mRNA expression level of CDH1 gene of the stably Zic5 gene-expressed line and the stably Flag-expressed line is shown in FIG. 5. As a result, it was shown that E-cadherin expression was reduced in the stably Zic5 gene-expressed line.
<Influence of Suppressing Zic5 Gene Expression on E-Cadherin Expression Level>

An mRNA level of CDH1 gene in a case of RNA-mediated Zic5 gene knockdown in the stably Zic5 gene-expressed line and the stably Flag-expressed line, was measured by qRT-PCR.

In the same manner as Example 1, the stably Zic5 gene-expressed line and the stably Flag-expressed line were transfected with siZIC5#2 described in Table 2 or a negative control, siRNA (siNeg#1). An mRNA level of CDH1 gene of the siRNA-transfected cells was measured by qRT-PCR in the same manner as above by using an mRNA level of GAPDH gene as an internal control.

TABLE 2

| siRNA | Targeting sequence | SEQ. NO. |
|---|---|---|
| siZic5 #1 | AAGATTCGAGGCTGTGACAAA | 5 |
| siZic5 #2 | GGCTGTGACAAATCCTACA | 6 |

TABLE 2-continued

| siRNA | Targeting sequence | SEQ. NO. |
|---|---|---|
| siNeg #1 | AATTCTCCGAACGTGTCACGT | 7 |
| siNeg #2 | ATCCGCGCGATAGTACGTA | 8 |

Figure 6:
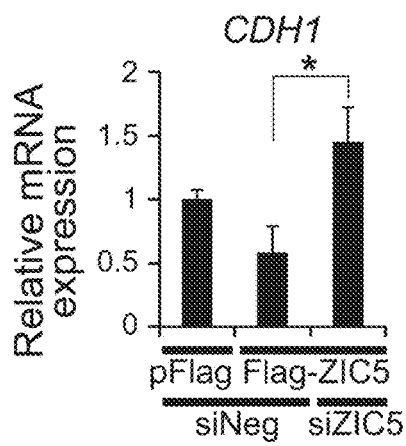
FIG. 6 illustrates measurement results of a relative mRNA expression level of CDH1 gene with GAPDH gene as an internal control of the stably Zic5 gene-expressed line and of the stably Flag-expressed line when Zic5 gene expression by RNA interference was suppressed in Example 2.

An average value (n=3) of a relative mRNA expression level of CDH1 gene of each cell is shown in FIG. 6. As a result, it was shown that a reduction of E-cadherin expression in the stably Zic5 gene-expressed line was recovered by RNA-mediated Zic5 gene knockdown.

<Endogenous ZIC5 Functions>

To elucidate the roles of endogenous ZIC5, the influence on RNA-mediated Zic5 gene knockdown was examined using the melanoma cell lines, SK-MEL-28 cells and A375 cells.

In the same manner as Example 1, each cell was transfected with siZIC5#1, siZIC5#2, siNeg#1, or siNeg#2 described in Table 2. An mRNA level of Zic5 gene, CDH1 gene, TYRP1 gene, TYR gene, and MMP2 gene of siRNA-transfected cells was measured by qRT-PCR in the same manner as above using an mRNA level of GAPDH gene as an internal control. For quantitation of an mRNA level of Zic5 gene, primers described in Table 3 were used.

TABLE 3

| Primer | Base Sequence | SEQ. NO. |
|---|---|---|
| ZIC5 forward | CACCAGTGACAAGCCCTACT | 9 |
| ZIC5 reverse | GAGTAACCAAGGGGTCCTGG | 10 |

When images of transmitted light of the cells transfected with siZIC5#2 or siNeg#2 are compared, it was observed that Zic5 gene knockdown induced a morphological change in A375 cells (not shown).

Figure 7:
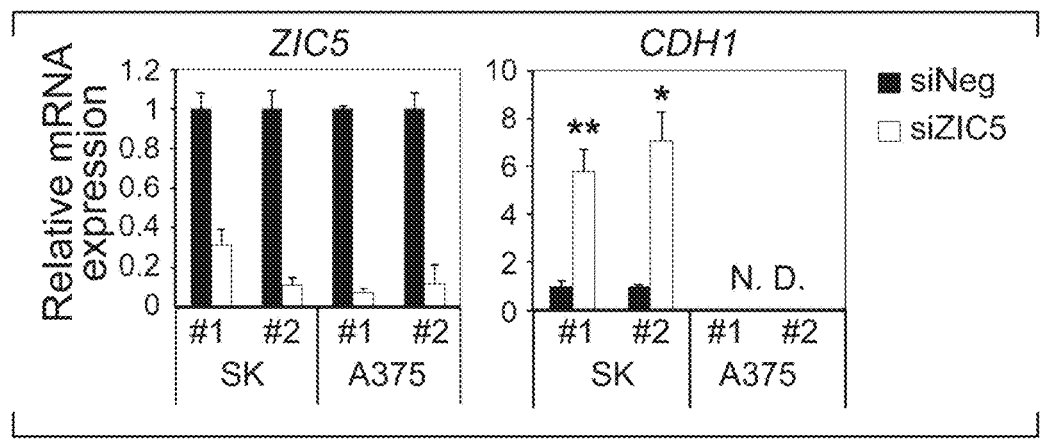
FIG. 7 illustrates measurement results of a relative mRNA expression level of Zic5 gene and CDH1 gene with GAPDH gene as an internal control of SK-MEL-28 cells and A375 cells transfected with siZIC5#1, siZIC5#2, siNeg#1, or siNeg#2 in Example 2.

An average value (n=3) of a relative mRNA expression level of Zic5 gene, CDH1 gene, TYRP1 gene, TYR gene, and MMP2 gene of each cell was examined (not shown). A measurement result of Zic5 gene and CDH1 gene of each cell is shown in FIG. 7. It was confirmed that a relative mRNA expression level of Zic5 gene was significantly reduced in the cells transfected with siZIC5#1 or siZIC5#2 in both of SK-MEL-28 cells and A375 cells. In the cells transfected with siZIC5#1 or siZIC5#2, increased expression of CDH1 gene, TYRP1 gene, and TYR gene, and MMP2 gene knockdown was induced. Based on these results, it is considered that Zic5 gene is a factor inducing E-cadherin suppression, promotion of cell dedifferentiation, and upregulation of matrix metalloproteinase (MMP2) in melanoma cells.

Example 3

Decreased expression of E-cadherin, dedifferentiation, and upregulation of matrix metalloproteinase (MMP2) induced by ZIC5 are all hallmarks of metastatic melanoma. Therefore, the influence of ZIC5 on motility, invasiveness, and proliferation, which are malignant phenotypes of melanoma cells, was examined next.

<Scratch Assay>

To analyze motility, a scratch assay was performed under a serum-free condition.

Specifically, the stably Zic5 gene-expressed line and the stably Flag-expressed line were cultured, confluent cells were scraped (scratched) with a tip of a yellow tip and then cultured in a serum-free medium. In the cells 24 hours after scratching, the number of migrated cells increased in the stably Zic5 gene-expressed line compared to the stably Flag-expressed line (not shown).

<Transwell Migration Assay>

To analyze motility, Transwell Migration Assay was performed under a serum-contained condition.

Figure 8:
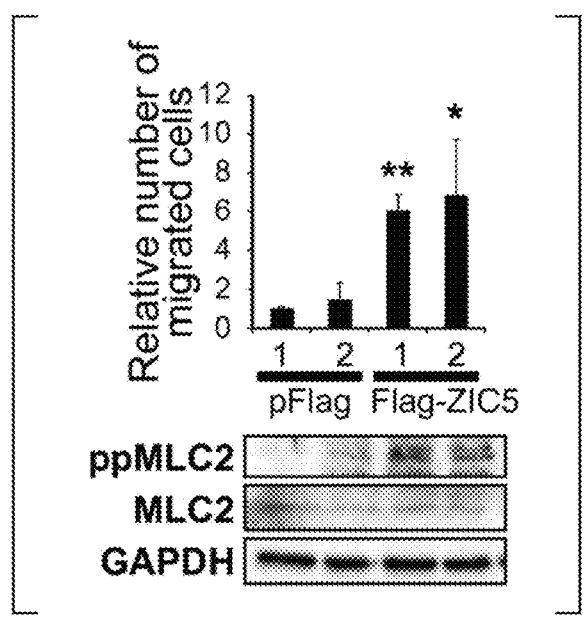
FIG. 8 illustrates count results of the number of migrated cells in Transwell Migration Assay (top) and western blotting images (bottom), performed with the stably Zic5 gene-expressed line and the stably Flag-expressed line in Example 3.

Specifically, the stably Zic5 gene-expressed line and the stably Flag-expressed line were seeded in a 24-well plate into which an insert with 8-µm sized pores (manufactured by BD Biosciences) was put and were cultured in RPMI 1640 medium containing 10% FBS, and then the number of migrated cells was counted. The count result is shown in FIG. 8 (top). As a result, the number of migrated cells greatly increased in the stably Zic5 gene-expressed line compared to the stably Flag-expressed line.

Myosin light chain 2 (MLC2) is known as an important factor for enhancing melanoma motility. It is known that MLC2 is activated through phosphorylation and enhances cell motility by enhancing actomyosin contraction (refer to NPLs 14 and 15). A protein level of phosphorylated MLC2 (ppMLC2), MLC2, and GAPDH of each cell was measured by western blotting. Western blotting was performed according to a method of Kanemaru et al. (refer to NPL 13) using anti-ppMLC2 antibody, anti-MLC2 antibody, and anti-GAPDH antibody (all manufactured by Cell Signaling).

The result of western blotting with each cell is shown at the bottom of FIG. 8. As a result, it was revealed that phosphorylation of MLC2 was enhanced in the stably Zic5 gene-expressed line compared to the stably Flag-expressed line.

Figure 9:
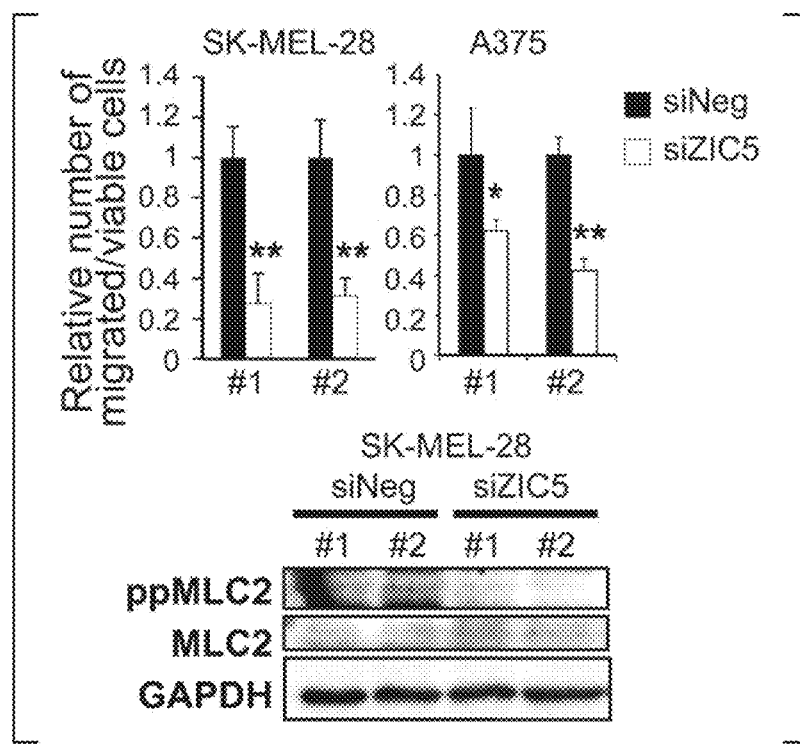
FIG. 9 illustrates count results of the number of migrated cells in Transwell Migration Assay (top) and western blotting images (bottom), performed with SK-MEL-28 cells and A375 cells transfected with siZIC5#1, siZIC5#2, siNeg#1, or siNeg#2 in Example 3.

Motility of melanoma cells in a case of siRNA-mediated knockdown of endogenous Zic5 gene was examined by performing Transwell Migration Assay. Specifically, SK-MEL-28 cells and A375 cells, which are melanoma cell lines, were transfected with siZIC5#1, siZIC5#2, siNeg#1, or siNeg#2 described in Table 2 in the same manner as Example 1. In the same manner as above, Transwell Migration Assay was performed with the cells transfected with each siRNA, and then the number of migrated cells was counted. The count result is shown in FIG. 9 (top). As a result, a decrease in cell migration rate by Zic5 gene knockdown was observed in both cells. The protein level of ppMLC2, MLC2, and GAPDH in the cells in which SK-MEL-28 cells were transfected with siRNA was measured by western blotting. The result of western blotting with SK-MEL-28 cells is shown at the bottom of FIG. 9. As a result, a reduction of ppMLC2 by Zic5 gene knockdown was confirmed.

<Transwell Invasion Assay>

Figure 10:
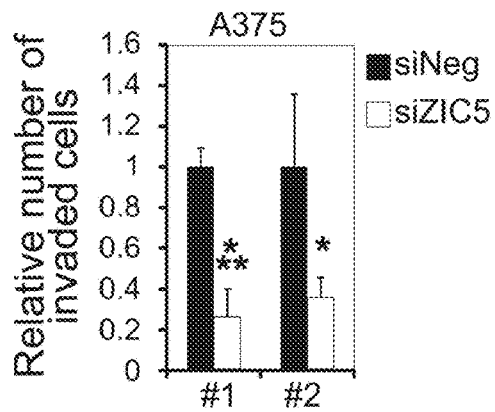
FIG. 10 illustrates count results of the number of invaded cells in Transwell Invasion assay performed with A375 cells transfected with siZIC5#1, siZIC5#2, siNeg#1, or siNeg#2 in Example 3.

Transwell Invasion Assay was performed according to a method of Hirano et al. (refer to NPL 16) using cell culture inserts added to 60 µL (2.5 mg/mL) of BD Matrigel Basement Membrane Matrix Growth Factor Reduced (manufactured by BD Biosciences). The number of cells that invaded Matrigel was counted. The count result is shown in FIG. 10. As a result, a decrease in cell invasion rate by Zic5 gene knockdown was observed.

<Transwell Migration Assay Under Suppression of MLC2 Phosphorylation>

Figure 11:
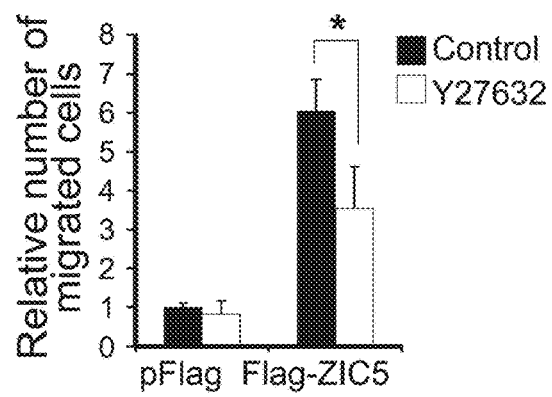
FIG. 11 illustrates count results of the number of migrated cells in Transwell Migration Assay performed with the stably Zic5 gene-expressed line and the stably Flag-expressed line which are treated or non-treated with a ROCK inhibitor (Y27632) in Example 3.

The influence of suppressing MLC2 phosphorylation on migration ability of cells was analyzed. Specifically, Transwell Migration Assay was performed in the same manner as above with the stably Zic5 gene-expressed line and the stably Flag-expressed line in a state of being treated or non-treated with a ROCK inhibitor (Y27632), and then the number of migrated cells was counted. The count result is shown in FIG. 11. As a result, an increase of migrated cells by Zic5 gene overexpression could be partially suppressed by suppressing of MLC2 phosphorylation through ROCK inhibitor treatment.

The protein level of ppMLC2, MLC2, and GAPDH in each cell was measured by western blotting in the same manner as above. As a result, a band of ppMLC2 detected by the stably Zic5 gene-expressed line not treated with the ROCK inhibitor was hardly detected in the stably Zic5 gene-expressed line treated with the ROCK inhibitor, and by ROCK inhibitor treatment, MLC2 phosphorylation, which was enhanced in the stably Zic5 gene-expressed line, was suppressed by ROCK inhibitor treatment (not shown).

Based on these results, it was revealed that ZIC5 is a factor promoting motility of melanoma cells, and the enhancement of MLC2 phosphorylation is the cause thereof.

<Cell Proliferation Assay>

Cell proliferation assay was performed to examine the influence of Zic5 gene on cell proliferation.

Figure 12:
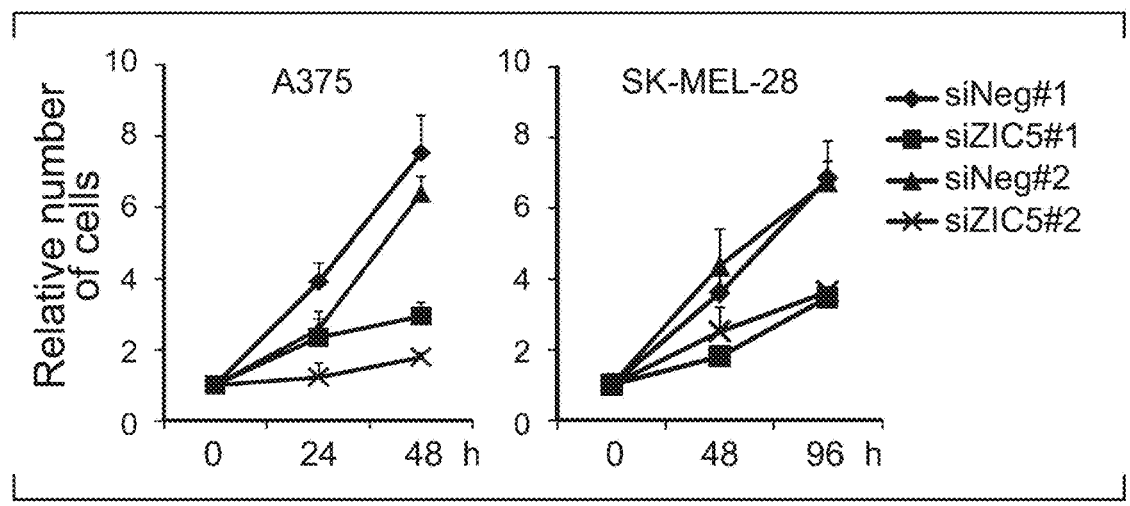
FIG. 12 illustrates results of measuring the cell number of A375 cells and SK-MEL-28 cells transfected with siZIC5#1, siZIC5#2, siNeg#1, or siNeg#2, over time in Example 3.

In cell proliferation assay, A375 cells and SK-MEL-28 cells transfected with siZIC5#1, siZIC5#2, siNeg#1, or siNeg#2 described in Table 2 in the same manner as Example 1 were plated at 1,000 to 2,000 cells/well in 96-well plates. The number of cells transfected with each siRNA was measured over time. Regarding counting the number of cells, cell nuclei were stained with Hoechst 33342 (manufactured by Dojindo, Kumamoto, Japan), and the total cell number in each well was counted by using an IN Cell Analyzer 2000 (manufactured by GE Healthcare, Piscataway, N.J.). An average value (n=3) of the number of cells of each cell is shown in FIG. 12. As a result, it was revealed that in the cells transfected with ZIC5#1 or siZIC5#2 in both of A375 cells and SK-MEL-28 cells, cell proliferation was slow and the proliferation rate of melanoma cells was reduced by Zic5 gene knockdown. The same tendency was observed in Colo829 cells and HT1144 cells (not shown).

Figure 13:
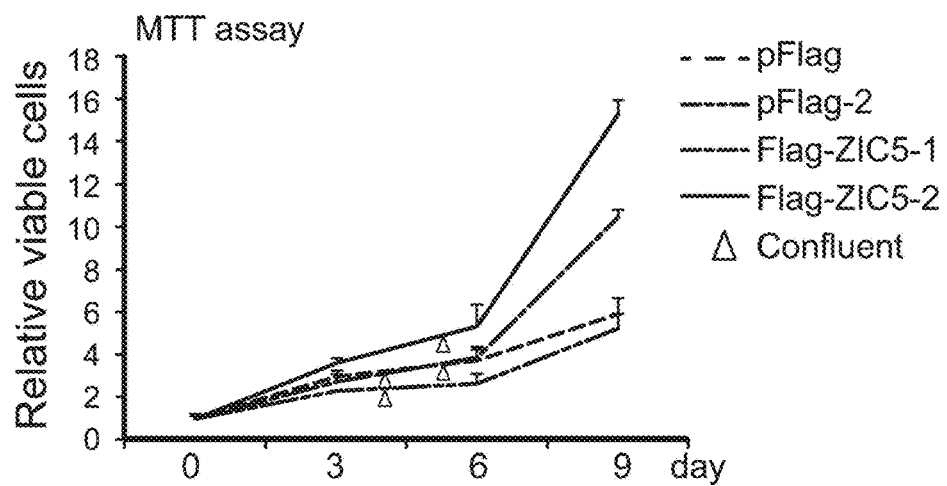
FIG. 13 illustrates measurement results of the relative number of viable cells in MTT assay performed with the stably Zic5 gene-expressed line and the stably Flag-expressed line in Example 3.

The stably Zic5 gene-expressed line and the stably Flag-expressed line were cultured for 9 days, MTT assay was performed over time, and the relative viable cell number was measured. The measurement result is shown in FIG. 13. In the drawing, "A" indicates a point where the cells became confluent. As a result, a phenomenon in which the cell number continues to increase even after the cell density became high in the stably Zic5 gene-expressed line was observed.

<Cell Cycle Analysis>

The influence of Zic5 gene on the cell cycle was examined by performing cell cycle analysis on the cells in which A375 cells were transfected with siZIC5#2 or siNeg#2 described in Table 2 in the same manner as Example 1.

Figure 14:
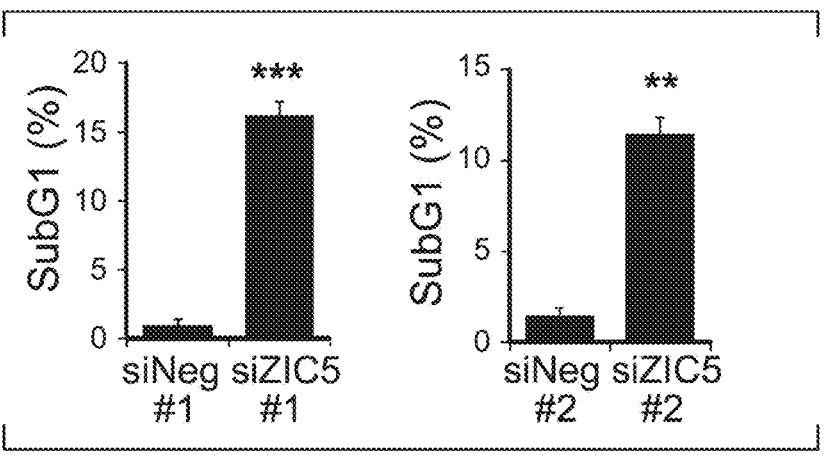
FIG. 14 illustrates a percentage (%) of cells in sub-G1 population of each cell of Example 3.

In cell cycle analysis, first, the cells were cultured in serum-free medium for 24 hours and then cultured in media containing 10% FBS for 24 hours. Next, the cells were fixed, stained with propidium iodide (PI), and then flow cytometry analysis (SH800, manufactured by Sony) was performed. The obtained data was analyzed using analysis software, FlowJo (manufactured by TOMY DIGITAL BIOLOGY, Tokyo, Japan). As a result, a sub-G1 population of cells increased in the cells in which Zic5 gene knockdown occurred. The same result was obtained in the cells transfected with siZIC5#1 or siNeg#1. Percentages (%) of sub-G1 population of the cell number are shown in FIG. 14. The statistical difference was determined using the Student's t-test (*: P<0.001, : P<0.01, *: P<0.05).

Based on these results, it was revealed that Zic5 gene is a factor for promoting proliferation of melanoma cells.

Example 4

Based on the results so far, it was confirmed that Zic5 gene promotes cell proliferation, migration ability, and invasiveness of melanoma cells, and therefore the proliferation and metastasis of melanoma in a living body was examined.

<Production of shZic5 Line and shNeg Line>

A shZic5 line in which shRNA-transfected plasmid with respect to Zic5 gene was stably inserted to A375 cells having a high level of metastatic ability, and a negative control line (shNeg line) in which a negative control, shRNA-transfected plasmid was inserted to the A375 cells were produced.

In the shNeg line, A375 cells were transfected with pSIREN-RetroQ-ZsGreen (manufactured by Clontech, Palo Alto, Calif.), which is a shRNA expression vector, and in a shZic5-1 line or anshZic5-2 line, the cells were transfected with shRNA for Zic5 targeting a base sequence described in Table 4 which is inserted to pSIREN-RetroQ-ZsGreen. The transfection with shRNA was performed in the same manner as in the transfection with plasmid. After the shRNA-transfected cells were limiting-diluted, GFP-positive clones were isolated and used as stably expressed lines.

TABLE 4

| shRNA | Targeting sequence | SEQ. NO. |
|---|---|---|
| shZIC5-1 | GGCTGTGACAAATCCTACA | 11 |
| shZIC5-2 | GATTCGAGGCTGTGACAAA | 12 |

<Decreased Expression of Zic5 Gene in Living Body and Proliferation and Metastasis of Human Melanoma Cells>

A cell suspension in which 10,000,000 of the shNeg lines, the shZic5-1 lines, or the shZic5-2 lines were suspended in 0.1 mL of PBS was subcutaneously injected into 5-week-old BALB/c nu/nu nude mice (purchased from CLEA, Tokyo, Japan). Tumor volume (V) formed was measured every 3 or 4 days after the subcutaneous injection based on the following formula. In the formula, "A" represents a largest diameter of the tumor and "B" represents a smallest diameter of the tumor.

$$V = \tfrac{1}{2}(A \times B^2)$$

The measurement result is shown in FIG. 15. FIG. 15(A) is the result of the tumor volume (V) measured, and FIG. 15(B) is a weight of the tumor on the 34th day after the transplantation. The statistical difference was determined using the Dunnett's multiple comparisons of means test (***: P<0.001). As a result, in a case where the shZic5-1 line or the shZic5-2 line was transplanted, tumors in a living body hardly grew, and a remarkable suppression of tumor proliferation rate was confirmed. As a result of measuring a weight of an excised tumor, it was revealed that the tumor weight was significantly reduced in the shZic5-1 line and the shZic5-2 line compared to the shNeg line. That is, it was found that tumor proliferation was suppressed also in the living body by Zic5 gene knockdown.

<Measurement of Lung Metastatic Ability>

The shNeg lines, the shZic5-1 lines, or the shZic5-2 lines were tail vein-injected into 6-week-old BALB/c nu/nu nude mice (purchased from CLEA, Tokyo, Japan) to be transplanted, and on 2.5th month after transplantation, lung metastatic ability was examined. Specifically, the number of nodules formed in the lung was measured. Furthermore, in order to quantify a degree of invasiveness of human melanoma cells in the mouse lung, an mRNA level of human GAPDH gene in mouse lung tissues was measured. An mRNA level of human GAPDH gene was measured by qRT-PCR and normalized to an mRNA level of mouse GAPDH gene.

The measurement result is shown in FIG. 16. FIG. 16(A) shows the measurement result of the number of nodules formed in the lung, and FIG. 16(B) shows the measurement result of mRNA level of human GAPDH gene normalized to an mRNA level of mouse GAPDH gene in the lung. The statistical difference was determined using the Mann-Whitney's U-test. As a result, the number of tumors formed in the lung was significantly reduced in the mouse to which the shZic5-1 line or the shZic5-2 line was transplanted. In addition, it was shown that an mRNA level of human GAPDH gene contained in the mouse lung was greatly reduced in the mouse into which the shZic5-1 line or the shZic5-2 line is inoculated compared to the shNeg line. Based on these results, it was suggested that ZIC5 is a factor for promoting metastasis of melanoma cells.

Example 5

ZIC5 belongs to C2H2 type zinc finger domain containing a Zic family group which contains Zic1 to 5. Zic1 to 3 have been reported to function as a transcription factor and target genes, whereas Zic4 and Zic5 have not been reported to function as a transcription factor and target genes. However, it is shown that mouse the Zic5 zinc finger domain (Zic5 ZF) as well as other Zics have an ability to bind to Gli binding sequence (GBS) and several mutation sequences of GBS (refer to NPL 17).

When a promoter region of gene in which expression is altered according to ZIC5 was examined, a sequence, GGGCGGT, to which mouse Zic5 ZF binds, was present in a promoter region of E-cadherin. A possibility that ZIC5 binds to an E-cadherin promoter to regulate transcription was verified with a gel shift assay (electrophoretic mobility shift assay, EMSA).

FIG. 17 shows an alignment view of base sequences of oligonucleotide probes used in EMSA. In the drawing, the area surrounded by square brackets is the putative zinc finger domain binding sequence. In addition, in the drawing, "M5" is a base sequence in which one base substitution mutation is introduced into GBS, and "pCDH1" is a promoter region of human CDH1 gene (E-cadherin promoter).
<EMSA>

Specifically, first, the zinc finger domain of human ZIC5 was amplified by PCR using a forward primer and a reverse primer composed of a base sequence described in Table 5, and subcloned into pGEX-6P (manufactured by Amersham pharmacia), and therefore a ZIC5 ZF (GST-ZIC5 ZF) expression vector fused with GST was prepared. The GST-ZIC5 ZF was transfected with E. coli BL21 line, and the expressed GST-ZIC5 ZF was purified using glutathione sepharose beads (manufactured by GE Healthcare).

TABLE 5

| Primer | Base Sequence | SEQ. NO. |
|---|---|---|
| ZIC5-ZF forward | CCCGGATCCGTGAATCACGTCACGGTGGAG | 13 |
| ZIC5-ZF reverse | CCCCTCGAGTTAGCAGTGAATCTTCATGTGC TTCC | 14 |

The purified GST-ZIC5 ZF and three probes formed of biotin-labeled oligonucleotides composed of the base sequences described in FIG. 17 (manufactured from Hokkaido System Science) (SEQ. NO. 15 to 17) were each incubated in binding buffer (40 mM Tris-HCl, pH 8.0, 7 mM MgCl$_2$, 3 mM DTT, 0.1 mg/mL bovine serum albumin, 90 mM NaCl, and 150 ng poly(dI-dC)), and complexes formed were separated by 6% polyacrylamide gel electrophoresis (electrophoresis buffer: 0.5×TBE buffer (pH 8)). The separated complexes were detected using HRP (horseradish peroxidase)-conjugated streptavidin. The band patterns detected by staining the gel subjected to electrophoresis with HRP-conjugated streptavidin are shown in FIG. 18.

Figure 18:
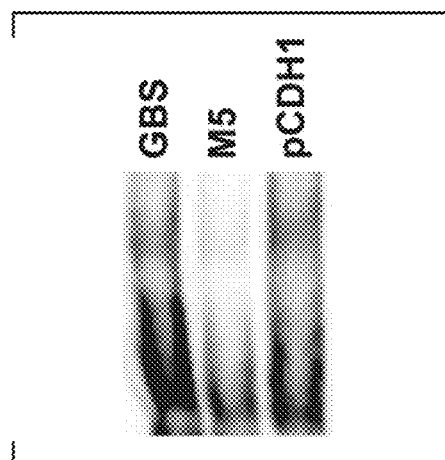
FIG. 18 illustrates stained images in which gel subjected to electrophoresis of EMSA is stained with HRP-labeled streptavidin of Example 5.

As shown in FIG. 18, it was revealed that human Zic5 ZF binds to GBS similarly to mouse Zic5 ZF, but does not bind to M5 into which mutation was introduced. Furthermore, binding to an E-cadherin promoter sequence containing putative Zic5 ZF binding sequence was also confirmed. As a result, it was revealed that human Zic5 ZF has the same characteristics as those of mouse Zic5 ZF and can bind to a sequence in an E-cadherin promoter region.
<Chromatin Immunoprecipitation (ChIP) Assay>

Next, to confirm the binding of human Zic5 (full length) to an E-cadherin promoter region in cells, ChIP assay was performed.

Specifically, after HA-tagged Zic5 (Zic5-HA) was forcibly expressed in HeLa cells, the cells were treated with 1% formaldehyde solution for 3 hours at 4° C. to be fixed, and then glycine was added to a final concentration of 125 mM and left to stand for 10 minutes, and then reactions were stopped. Next, the cells were washed with PBS containing 2% FBS, lysed with lysis buffer (5 mM PIPES (pH 8.0), 85 mM KCl, 0.5% NP-40), and the obtained lysate was added to MNase (manufactured by TaKaRa, Shiga, Japan) and treated for 30 minutes at 37° C. The MNase-treated lysate was centrifuged at 10,000 rpm for 10 minutes at 4° C. and the supernatants were collected.

The supernatants were diluted with ChIP dilution buffer (50 mM Tris-Hcl (pH 8), 167 mM NaCl, 1.1% Triton X-100), and then added to mouse IgG or anti-HA antibody (manufactured by Sigma Aldrich), and immunoprecipitation was performed at 4° C. overnight. Immuno-complexes formed were collected with Protein A/G beads and washed with RIPA buffer (100 mM Tris-HCl (pH 8.0), 300 mM NaCl, 2 mM EDTA (pH 8.0), 2% Triton X-100, 0.2% SDS, 0.2% sodium deoxycholate) and LiCl buffer (10 mM Tris-HCl (pH 8.0), 0.25 M LiCl, 1 mM EDTA (pH 8.0), 0.5% NP-40, 0.5% sodium deoxycholate). The protein-DNA complexes obtained were reverse-crosslinked by heating for 4 hours at 65° C., followed by proteinase K treatment, and then the resulting DNA was purified using a PCR Purification kit (manufactured by Qiagen). The DNA samples obtained were amplified by PCR using the primers described in Table 6 to be quantified. A region locating at the downstream of the same chromosome with E-cadherin was a negative control.

TABLE 6

| Primer | Base Sequence | SEQ. NO. |
|---|---|---|
| pCDH1 forward | TAGAGGGTCACCGCGTCTAT | 18 |
| pCDH1 reverse | ATTGGCTGAGGGTTCACCTG | 19 |
| Forward negative control | GCAGTGGGATAGGAGCAGAC | 20 |
| Reverse negative control | CCGTGGCTACTGGATGTGTC | 21 |

Figure 19:
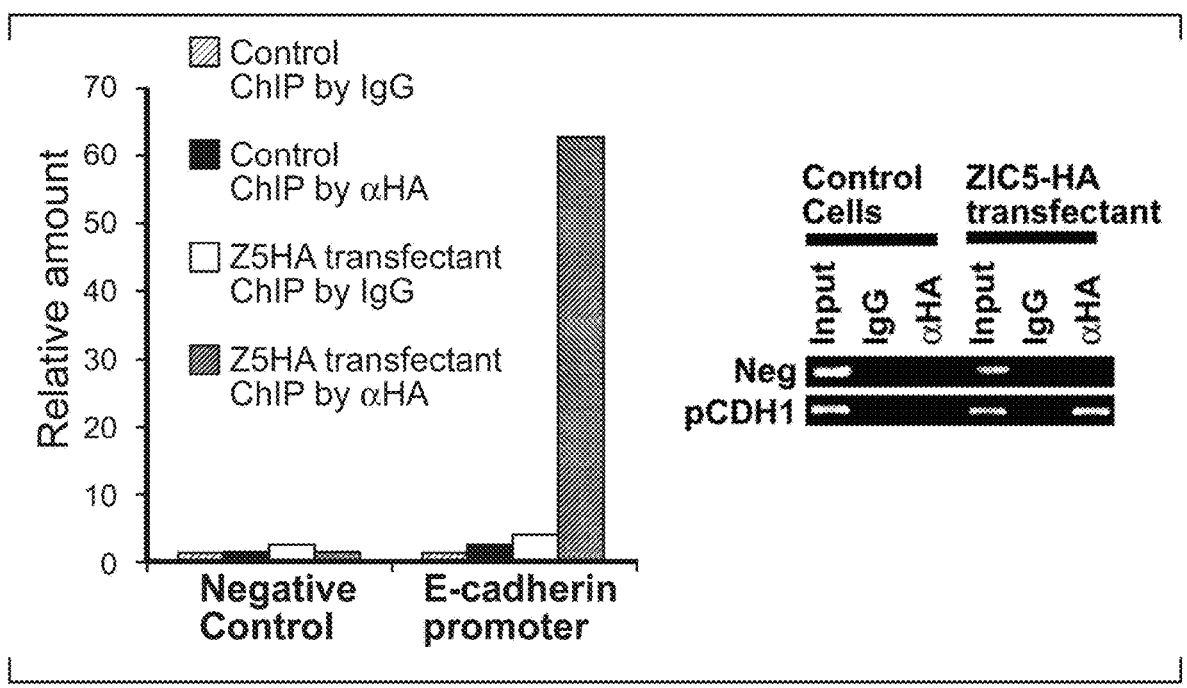
FIG. 19 illustrates a measurement result of a relative level of DNA precipitated with mouse IgG or anti-HA antibody by chromatin immunoprecipitation in Example 5.

The quantitative result is shown in FIG. 19 (left drawing) and a drawing of electrophoresis of each DNA is shown in FIG. 19 (right drawing). As a result, coprecipitation with the E-cadherin promoter region was confirmed only in the sample in which the cells in which Zic5-HA was forcibly expressed were subjected to the immunoprecipitation using anti-HA antibody. DNA in the negative control region locating at the downstream of the same chromosome with E-cadherin was not detected, and therefore it was possible to confirm the specificity of coprecipitation of Zic5-HA with the E-cadherin promoter region.

<Luciferase Reporter Assay>

To examine whether ZIC5 actually regulates E-cadherin promoter activity, a plasmid linked to E-cadherin promoter-driven luciferase was produced, and therefore luciferase assay was performed.

Specifically, first, the CDH1 promoter region was amplified by PCR using pCDH1 forward primer and pCDH1 reverse primer described in Table 7, and sub-cloned into XhoI-NcoI region of pGL3-basic vector (manufactured by Promega), and therefore, the luciferase reporter construct (pCDH1-Luc) was produced. In addition, as an internal control, the phRL-TK plasmid (manufactured by Promega) of Renilla luciferase was used.

Figure 20:
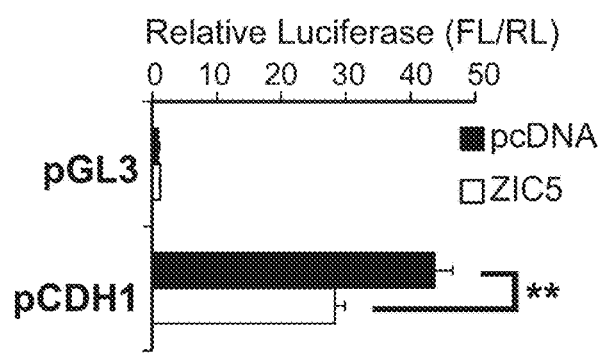
FIG. 20 illustrates results of luciferase reporter assay in Example 5.

HEK293 cells were transiently transfected with pCDH1-Luc and phRL-TK using the Lipofectamine 2000 (manufactured by Invitrogen Corporation). Luciferase activity was measured using the Dual-luciferase Reporter Assay System (manufactured by Promega). The statistical difference was determined using the Student's t-test (*: $P<0.001$, : $P<0.01$, *: $P<0.05$). The measurement result (n=3) is shown in FIG. 20. As a result, it was shown that E-cadherin promoter activity decreased in a case of forcibly expressing Zic5.

Figure 21:
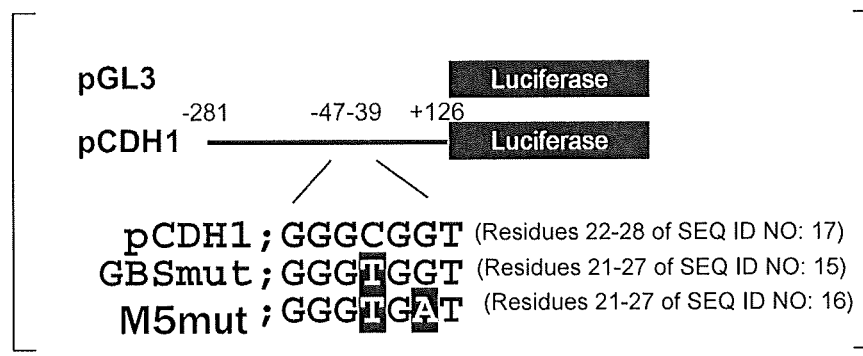
FIG. 21 is an alignment view of base sequences of an E-cadherin promoter region (pCDH1) before introducing mutations and mutants GBSmut and M5mut into which one base substitution mutation was introduced in Example 5.

To verify whether suppression of E-cadherin promoter activity by ZIC5 is performed through a putative ZIC5 binding sequence shown in FIG. 17, one base substitution mutation was introduced into putative ZIC5 binding sequence of the E-cadherin promoter, and therefore luciferase assay was performed. FIG. 21 shows a base sequence into which one base substitution mutation was introduced. A mutant GBS-mut is confirmed to be a mutant to which Zic5 ZF binds, and a mutant M5-mut is confirmed to be a mutant to which Zic5 ZF does not bind. The mutants, GBSmut and M5mut, in which one base substitution mutation shown in FIG. 21 was introduced into the reporter construct were produced using primers described in Table 7.

Figure 22:
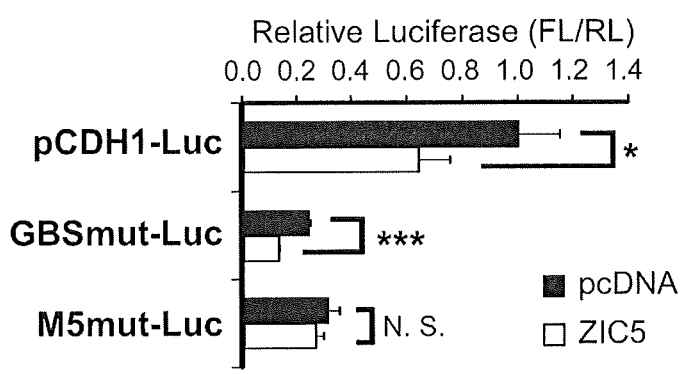
FIG. 22 illustrates results of luciferase reporter assay of pCDH1 before introducing mutations, mutants GBSmut, and M5mut in Example 5.

Luciferase reporter assay was performed in the same manner as above using the mutants produced. The measurement result (n=3) is shown in FIG. 22. As a result, activity of the promoter into which GBS-mut was introduced was suppressed by forcibly expressing ZIC5, but activity of the promoter into which M5-mut was introduced was not suppressed. Based on the results above, it was revealed that ZIC5 recognizes the GGGCGGT sequence in the E-cadherin promoter and binds thereto, and thus suppresses the activity of this promoter.

Example 6

Based on the results above, it was revealed that ZIC5 functions as a transcription factor regulating E-cadherin expression, but ZIC5-induced phenotypic change of melanoma cannot be explained only with regulation of E-cadherin expression. Therefore, microarray analysis was performed to comprehensively investigate alteration of gene expression by ZIC5.

<Microarray Analysis>

A375 cells or SK-MEL-28 cells were transfected with siZIC5 or siNeg described in Table 2 in the same manner as Example 1. The cells were collected 48 hours after siRNA transfection and RNA was extracted. Total RNA from each sample (1 µg) was subjected to microarray analysis using GeneChip Human Genome U133 Plus 2.0 Array (manufactured by Affymetrix, Santa Clara, Calif., USA) according to the product protocols. Quantitative normalization was performed according to an RNA expression level obtained from array data. Heat map visualization was performed using Mev (MultiExperiment Viewer). Pathway analysis was performed using DAVID (NPL 18).

When Zic5 expression was suppressed in A375 cells and SK-MEL-28 cells, 913 genes were identified to be upregulated 1.5-fold or more in both cells, whereas 302 genes were identified to be downregulated half or less in both cells. When pathway analysis was performed to investigate the phenomena associated with these altered genes, it was found that Glioma, Focal adhesion, and Tight junction-related genes are contained in large amounts therein (not shown).

<Analysis of Relationship with Focal Adhesion-Related Factor>

Because phosphorylation of focal adhesion kinase (FAK), which is activated at Focal adhesion, has been associated with melanoma malignancy (refer to NPL 19), FAK change by ZIC5 was examined. Furthermore, focusing on Integrin, alpha 6 (ITGA6) and platelet-derived growth factor D (PDGFD) among the Focal adhesion-related genes in the altered genes by Zic5 knockdown, change in cells was examined. Specifically, a level of phosphorylated FAK (pFAK), total FAK (FAK), ITGA6, pro-PDGFD, and β-actin in A375 cells transfected with siZIC5 or siNeg was assessed by western blotting. Western blotting was performed in the same manner as above except that anti-pFAK antibody (manufactured by Signalway Antibody), anti-FAK antibody (manufactured by Acris), anti-β-actin antibody (manufac-

TABLE 7

| Primer | Base Sequence | SEQ. NO. |
|---|---|---|
| pCDH1 forward | CACACTCGAGCACCACTGCACTCCAGCTTGG | 22 |
| pCDH1 reverse | CTCCAAGGGCCCATGGCTGG | 23 |
| M5mut forward | CTCCGGGGCTCACCTGGCT | 24 |
| M5mut reverse | GCATCACCCCCCGTACCGCTGATTGGCTGAG | 25 |
| GBSmut forward | CTCCGGGGCTCACCTGGCT | 26 |
| GBSmut reverse | GCACCACCCCCCGTACCGCTGATTGGCTGAG | 27 | tured by Sigma), anti-ITGA6 antibody (manufactured by GeneTex), and anti-PDGFD antibody (manufactured by Santa Cruz) were used. As a result, it was revealed that the phosphorylation of FAK significantly decreased in the cells in which Zic5 expression was suppressed. In addition, a tendency for the expression level of ITGA6 and pro-PDGFD also to have decreased was observed (not shown).

Figure 23:
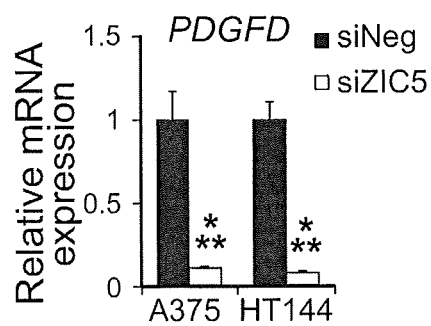
FIG. 23 illustrates measurement results of a relative mRNA expression level of PDGFD gene in A375 cells and HT144 cells transfected with siZIC5 or siNeg in Example 6.

The expression level of PDGFD gene in a case where A375 cells and HT144 cells were transfected with siZIC5 or siNeg described in Table 2 in the same manner as Example 1 was assessed by performing qRT-PCR using primers shown in Table 10. An mRNA level of PDGFD gene in each cell was normalized to an mRNA level of ACTB (β-actin) gene. The result of calculating a relative mRNA expression level of PDGFD gene (expression level of the cells transfected with siNeg was set to 1) (n=3) is shown in FIG. 23. The statistical difference was determined using the Student's t-test (*: $P<0.001$, : $P<0.01$, *: $P<0.05$). As a result, PDGFD gene expression was significantly reduced by Zic5 gene knockdown.

Figure 24:
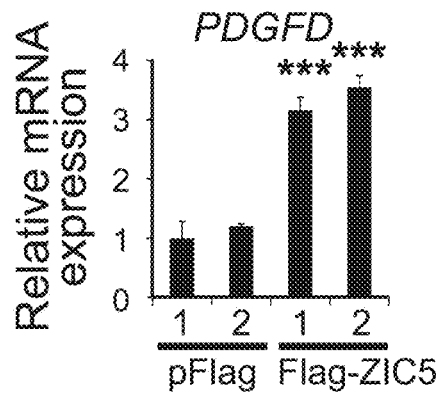
FIG. 24 illustrates measurement results of a relative mRNA expression level of PDGFD gene in the stably Zic5 gene-expressed line and the stably Flag-expressed line in Example 6.

In addition, the expression level of PDGFD gene in the cells of the stably Zic5 gene-expressed line and the stably Flag-expressed line was assessed in the same manner. The result of calculating a relative mRNA expression level of PDGFD gene (expression level of the cells transfected with siNeg#1 was set to 1) (n=3) is shown in FIG. 24. The statistical difference was determined using the Dunnett's multiple comparisons of means test (***: $P<0.001$). As a result, it was confirmed that a relative mRNA expression level of PDGFD gene in the stably Zic5 gene-expressed line was higher compared to that in the stably Flag-expressed line, and PDGFD gene expression was upregulated by Zic5 gene overexpression.

In addition, A375 cells and SK-MEL-28 cells were transfected with siNeg#1 described in Table 1, and siPDGFD#1 and siPDGFD#2 described in Table 8 in the same manner as Example 1 to examine the influence on PDGFD gene knockdown. As a result, in the cells transfected with siPDGFD#1 or siPDGFD#2 in both cells, morphological change occurred (not shown). That is, it was found that PDGFD knockdown in the melanoma cell lines induces morphological change in cells.

TABLE 8

| siRNA | Targeting sequence | SEQ. NO. |
|---|---|---|
| siPDGFD #1 | CAGGAATTACTCGGTCAATAT | 28 |
| siPDGFD #2 | AAGGTATATCATCAACTTCTA | 29 |
| siITGA6 #1 | CACGCGGATCGAGTTTGATAA | 30 |

In addition, the number of cells of each cell after siRNA transfection was counted over time, and a relative cell number in which the number of cells on the $1^{st}$ day after siRNA transfection was set to 1 was calculated to examine a proliferation property. As a result, it was found that the cell proliferation was suppressed in the cells transfected with siPDGFGD similarly to the cells transfected with siZic5, and the cell proliferation was suppressed by PDGFD gene knockdown in the melanoma cell line (not shown). The suppression of the cell proliferation by PDGFD gene knockdown was also observed in Colo829 cells and H1144 cells (not shown). Furthermore, a cell cycle of each cell was examined with respect to A375 cells. An average value (SD) of percentages (%) of cells in G1 population, S population, and G2M population of each cell is shown in Table 9. The statistical difference was determined using the Dunnett's multiple comparisons of means test (*: $P<0.001$, : $P<0.01$, *: $P<0.05$). As a result, percentages of cells in the S population and G2M population of A375 cells were reduced by PDGFD gene knockdown.

TABLE 9

|  | siNeg (%) | siPDGFD#1 (%) | siPDGFD#2 (%) |
|---|---|---|---|
| G1 | 65.9 (4.5) | 71.6 (0.23) | 74 (0.55) * |
| S | 10.2 (1) | 8.1 (0.38) * | 6.6 (0.49) ** |
| G2M | 20.7 (1.6) | 18.6 (0.25) | 17.7 (0.58) * |

Figure 25:
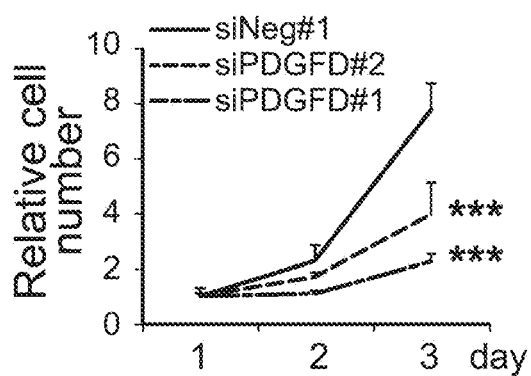
FIG. 25 illustrates results of measuring the cell number of A375 cells transfected with siPDGFD#1, siPDGFD#2, or siNeg#1, over time in Example 6.

In addition, the number of cells of A375 cells transfected with siPDGFD#1, siPDGFD#2, or siNeg#1 was successively counted. A relative cell number in which the number of cells transfected with siNeg#1 of each cell was set to 1 is shown in FIG. 25. The statistical difference was determined using the Dunnett's multiple comparisons of means test (**: $P<0.01$, *: $P<0.05$). As a result, a decrease in cell proliferation rate was induced in A375 cells by PDGFD gene knockdown.

Figure 26:
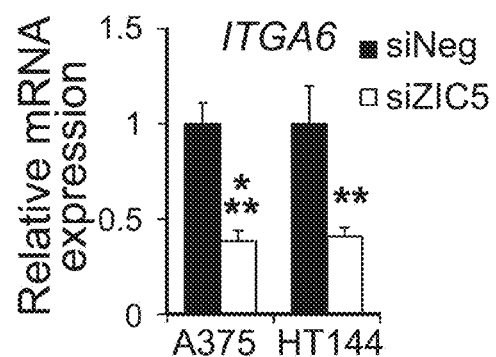
FIG. 26 illustrates measurement results of a relative mRNA expression level of ITGA6 gene in A375 cells and HT144 cells transfected with siZIC5 or siNeg in Example 6.

The expression level of ITGA6 gene in a case where A375 cells and HT144 cells were transfected with siZIC5 or siNeg described in Table 2 in the same manner as Example 1, was assessed by performing qRT-PCR using primers shown in Table 10. An mRNA level of ITGA6 gene in each cell was normalized to an mRNA level of ACTB (β-actin) gene. The result of calculating the relative mRNA expression level of ITGA6 gene (expression level of the cells transfected with siNeg was set to 1) (n=3) is shown in FIG. 26. The statistical difference was determined using the Student's t-test (*: $P<0.001$, : $P<0.01$, *: $P<0.05$). As a result, ITGA6 gene expression was significantly reduced by Zic5 gene knockdown.

Figure 27:
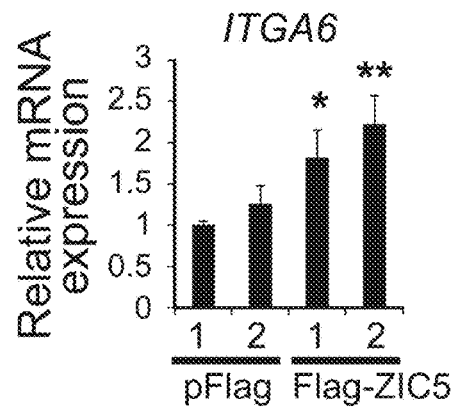
FIG. 27 illustrates measurement results of a relative mRNA expression level of ITGA6 gene in the stably Zic5 gene-expressed line and the stably Flag-expressed line in Example 6.

In addition, the expression level of ITGA6 gene in the cells of the stably Zic5 gene-expressed line and the stably Flag-expressed line was examined in the same manner. The result of calculating a relative mRNA expression level of ITGA6 gene (expression level of the cells transfected with siNeg#1 was set to 1) (n=3) is shown in FIG. 27. As a result, it was confirmed that a relative mRNA expression level of ITGA6 gene in the stably Zic5 gene-expressed line was higher compared to that in the stably Flag-expressed line, and ITGA6 gene expression was upregulated by Zic5 gene overexpression.

Figure 28:
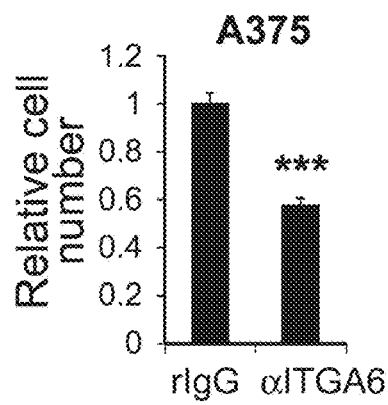
FIG. 28 illustrates measurement results of a relative cell number of A375 cells treated with rat IgG or anti-ITGA6 antibody in Example 6.

In addition, A375 cells were treated with an antibody solution of rat IgG or anti-ITGA6 antibody (20 μg/mL) for 72 hours, and then the number of cells was counted. The result of a relative cell number (n=3) in which the number of cells of the cells treated with rat IgG was set to 1 is shown in FIG. 28. The statistical difference was determined using the Student's t-test (*: $P<0.001$, : $P<0.01$, *: $P<0.05$). As a result, a decrease in cell proliferation was induced in the cells in which ITGA6 was neutralized by anti-ITGA6 antibody. In addition, a decrease in cell proliferation was also induced in the cells in which ITGA6 gene knockdown occurred by siITGA6 transfection (not shown). On the other hand, influence of ITGA6 gene knockdown on cell migration rate was hardly observed (not shown).

In addition, the number of cells in a case where an hITGA6-overexpressed line which is transfected with hITGA6 expression vector in which cDNA of human ITGA6 gene was inserted to plasmid pcDNA, and is selected by G418 treatment, and a pcDNA line (negative control) which is transfected with pcDNA, an empty vector, and is selected by G418 treatment, were transfected with siZIC5 or siNeg described in Table 2 in the same manner as Example 1, was counted. As a result, it was shown that a decrease in the number of cells by siZIC5 transfection was partially recovered in the hITGA6-overexpressed lines (not shown).

Figure 29:
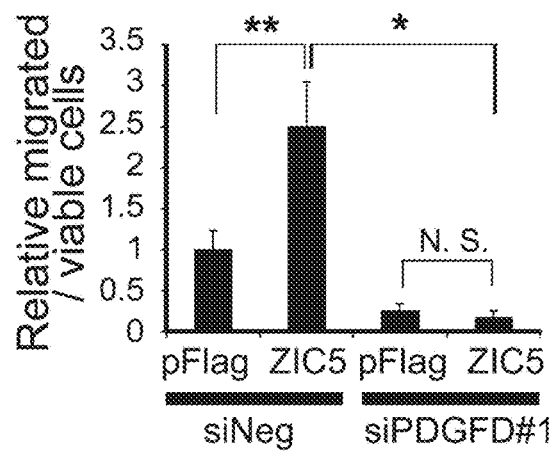
FIG. 29 illustrates measurement results of a relative number of migrated cells in Transwell Migration Assay performed with cells of the stably Zic5 gene-expressed line and the stably Flag-expressed line, which are transfected with siPDGFD#1 or siNeg#1 in Example 6.

In addition, with respect to the cells of the stably Zic5 gene-expressed line and the stably Flag-expressed line were transfected with siNeg#1 described in Table 1 and siPDGFD#1 described in Table 8 in the same manner as Example 1, Transwell Migration Assay was performed in the same manner as Example 2, and the number of migrated cells was counted. The number of migrated cells was normalized to a total number of viable cells. A relative cell number (n=3) in which the number of migrated cells transfected with siNeg#1 of each cell was set to 1 is shown in FIG. 29. The statistical difference was determined by the Tukey's multiple comparisons of means test (**: P<0.01, *: P<0.05). As a result, it was suggested that an increase in the number of migrated cells by Zic5 gene overexpression was completely suppressed in the cells transfected with siPDGFD#1. Based on the results, it was suggested that ZIC5 regulates cell migration through PDGFD expression.

In addition, the level of pFAK, total FAK, and β-actin in the cells transfected with siNeg#1 described in Table 1, or siPDGFD#1, siPDGFD#2, or siITGA6#1 described in Table 8 in the same manner as Example 1 was assessed by western blotting. As a result, similarly to Zic5 knockdown, PDGFD and ITGA6 knockdown reduced FAK phosphorylation, and therefore could be confirmed to be related to Focal adhesion (not shown).

TABLE 10

| Primer | Base Sequence | SEQ. NO. |
|---|---|---|
| ACTB (β-Actin) forward | GCCCTGGCACCCAGCACAAT | 31 |
| ACTB (β-Actin) reverse | GGAGGGGCCGGACTCGTCAT | 32 |
| PDGFD forward | AAGATTTCCAACCCGCAGCA | 33 |
| PDGFD reverse | TCCAGAGCATCCGCAATCAG | 34 |
| ITGA6 forward | GAGCCGTGGTTTTGCTGAAG | 35 |
| ITGA6 reverse | TGCCACCCATCCTTGTTGAG | 36 |

Example 7

Whether ZIC5 changes sensitivity to the BRAF inhibitor (PLX4032, vemurafenib) (manufactured by Selleckchem) was examined.

Specifically, first, the stably Zic5 gene-expressed line and the stably Flag-expressed line (control cells) were produced in the same manner as above using SK-MEL-28 cells.

Figure 30:
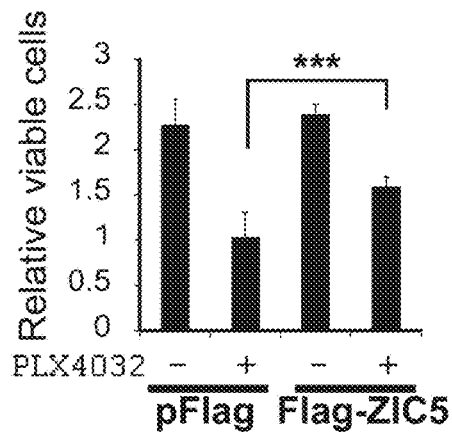
FIG. 30 illustrates measurement results of a relative cell number of the stably Zic5 gene-expressed line and the stably Flag-expressed line after being treated with PLX4032 or treated with DMSO in Example 7.
Figure 31:
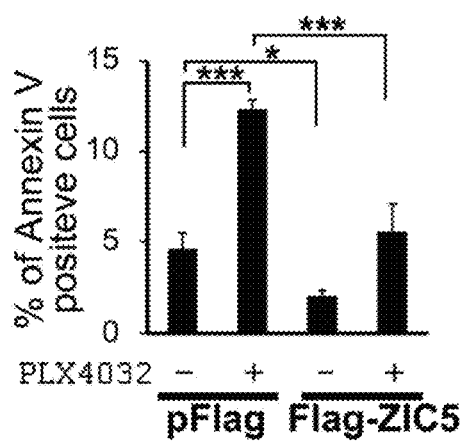
FIG. 31 illustrates measurement results of a percentage (%) of Annexin V-positive cells in the stably Zic5 gene-expressed line and the stably Flag-expressed line after being treated with a BRAF inhibitor, PLX4032 or treated with DMSO in Example 7.

The stably Zic5 gene-expressed line and the stably Flag-expressed line were each treated with PLX4032 at a final concentration of 10 μM for 48 hours, and the number of cells after the treatment was counted. PLX4032 was dissolved in DMSO to be used as a solution, and a line added to an equal amount of DMSO (DMSO treatment) was used as a control. The result of a relative cell number (n=3) in which the number of cells of the cells in which the stably Flag-expressed line was treated with PLX4032 (in the drawing, "+" on the "PLX4032" section, the same applies to the following examples), or the cells treated with DMSO (in the drawing, "−" on the "PLX4032" section, the same applies to the following examples) was set to 1 is shown in FIG. 30. The statistical difference was determined by the Tukey's multiple comparisons of means test (**: P<0.01, *: P<0.05). As a result, a decrease in the number of cells by PLX4032 treatment was alleviated in the stably Zic5 gene-expressed line. In addition, with respect to these cells, a percentage of apoptotic cells after PLX4032 treatment was detected by using FITC labeled Annexin V (manufactured by MBL, Nagoya, Japan). The result of percentage (%) of Annexin V-positive cells (cells stained with Annexin V) (n=3) in each cell is shown in FIG. 31. As a result, it was shown that induction of apoptosis by PLX4032 treatment was significantly reduced by Zic5 gene overexpression.

The percentage of Annexin V-positive cells was measured as follows. First, FITC labeled Annexin V (manufactured by MBL, Nagoya, Japan) and Hoechst33342 were added to each cell and incubated for 40 minutes. Next, a stained state of the incubated cells was analyzed by using DAPI filter and FITC filter of an imaging cytometer, "In Cell Analyzer 2000" (manufactured by GE healthcare). Percentage (%) of DAPI-stained all cells (DAPI-positive cells) to Annexin V-stained cells (Annexin V-positive cells) was determined by In Cell Analyzer Workstation 3.7 (manufactured by GE healthcare). The statistical difference was determined by the Tukey's multiple comparisons of means test (**: P<0.01, *: P<0.05).

Figure 32:
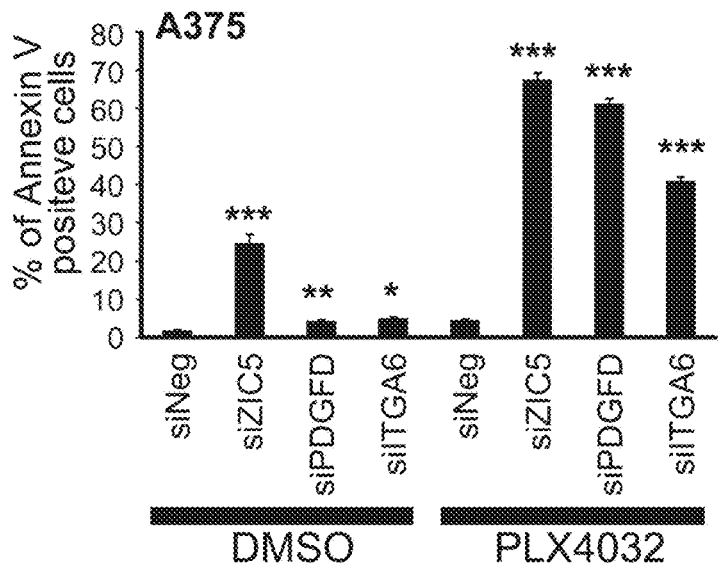
FIG. 32 illustrates measurement results of a percentage (%) of Annexin V-positive cells in A375 cells transfected with siNeg, siZIC5, siPDGFD, or siITGA6, after being treated with PLX4032 or treated with DMSO in Example 7.
Figure 33:
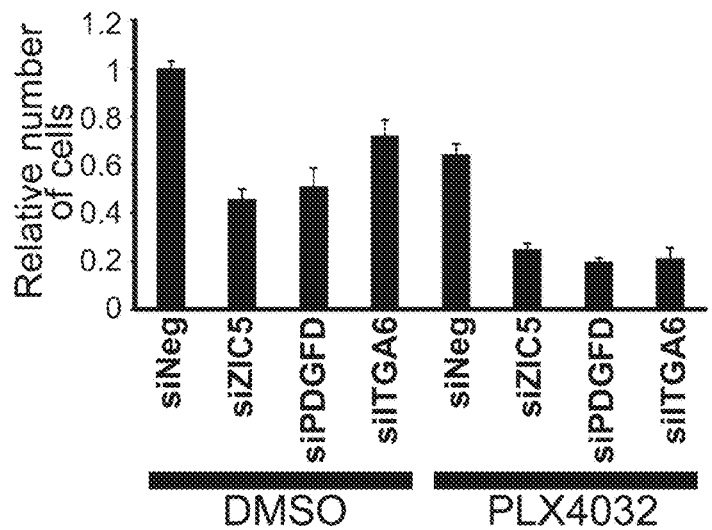
FIG. 33 illustrates measurement results of a relative cell number of A375 cells transfected with siNeg, siZIC5, siPDGFD, or siITGA6, after being treated with PLX4032 or treated with DMSO in Example 7.

Next, the influence of knockdown of endogenous ZIC5, and PDGFD and ITGA6, which are downstream factors, on a decrease in cell proliferation by PLX4032 and induction of apoptosis was examined. First, A375 cells were transfected with siNeg or siZIC5 described in Table 1, or siPDGFD or siITGA6 described in Table 8 in the same manner as Example 1, and then treated with DMSO or PLX4032 solution (which was dissolved in DMSO to become 5 μM) for 48 hours. Next, the treated cells were added to FITC labeled Annexin V (manufactured by MBL, Nagoya, Japan) and Hoechst33342 and incubated for 40 minutes. The result of percentage (%) of Annexin V-positive cells (n=3) in the incubated cells is shown in FIG. 32, and the result of a relative cell number (n=3) in which the number of cells of the cells transfected with siNeg was set to 1 is shown in FIG. 33. The statistical difference of the percentage of Annexin V-positive cells was determined using the Dunnett's multiple comparisons of means test (*: P<0.001, : P<0.01, *: P<0.05). As a result, it was revealed that induction of apoptosis by PLX4032 was synergistically upregulated by Zic5, PDGFD, and ITGA6 knockdown, and that a decrease in the number of cells by PLX4032 treatment was promoted by Zic5, PDGFD, and ITGA6 knockdown. The same results were also obtained in Colo829 cells (not shown).

Figure 34:
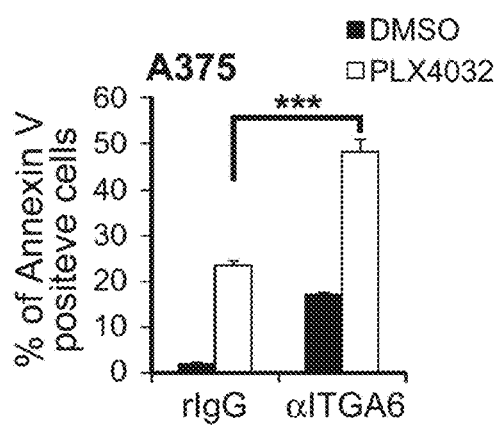
FIG. 34 illustrates measurement results of a percentage (%) of Annexin V-positive cells in A375 cells treated with rat IgG or anti-ITGA6 antibody, after being treated with PLX4032 or treated with DMSO in Example 7.

In addition, A375 cells were treated with an antibody solution of rat IgG or anti-ITGA6 antibody (20 μg/mL) together with DMSO or PLX4032 solution (which was dissolved to become 10 μM) for 48 hours. The result of percentage (%) of Annexin V-positive cells (n=3) in each cell after treatment is shown in FIG. 34. The statistical difference was determined using the Student's t-test (***: P<0.001). As a result, it was revealed that in the cells in which ITGA6 was neutralized by anti-ITGA6 antibody, induction of apoptosis can be synergistically induced with PLX4032. In addition, also in the cells each transfected with siZIC5 and siPDGFD, apoptosis could be synergistically induced with PLX4032 (not shown).

Figure 35:
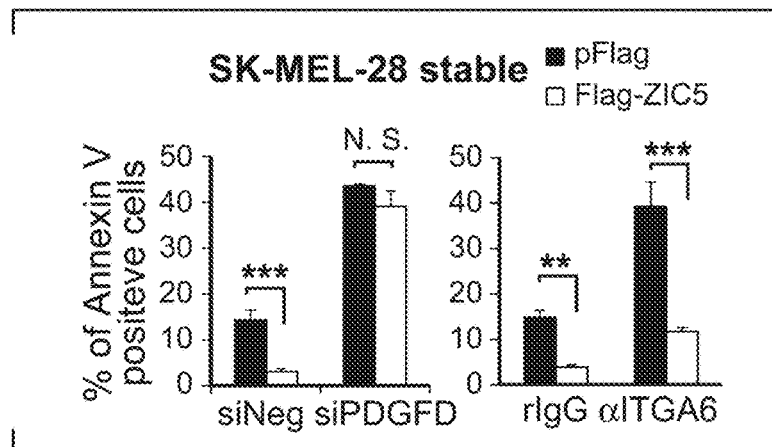
FIG. 35 illustrates measurement results of a percentage (%) of Annexin V-positive cells in the stably Zic5 gene-expressed line and the stably Flag-expressed line transfected with siNeg or siPDGFD (left drawing), and the stably Zic5 gene-expressed line and the stably Flag-expressed line treated with rat IgG or anti-ITGA6 antibody (right drawing), after being treated with PLX4032 in Example 7.

In addition, in the stably Zic5 gene-expressed line and the stably Flag-expressed line produced in Example 6, the cells transfected with siNeg described in Table 1 or siPDGFD described in Table 8 in the same manner as Example 1, and the cells added to an antibody solution of rat IgG or anti-ITGA6 antibody (20 µg/mL) were treated with PLX4032 solution (dissolved in DMSO to become 5 µM) for 48 hours. The result of percentage (%) of Annexin V-positive cells (n=3) in these cells is shown in FIG. 35. The statistical difference was determined by the Tukey's multiple comparisons of means test (**: P<0.01, *: P<0.05). As a result, it was revealed that the suppression of apoptosis by Zic5 gene overexpression was completely inhibited by PDGFD knockdown (FIG. 35 (left drawing) and partially inhibited by ITGA6 neutralizing antibody treatment (FIG. 35 (right drawing).

Figure 36:
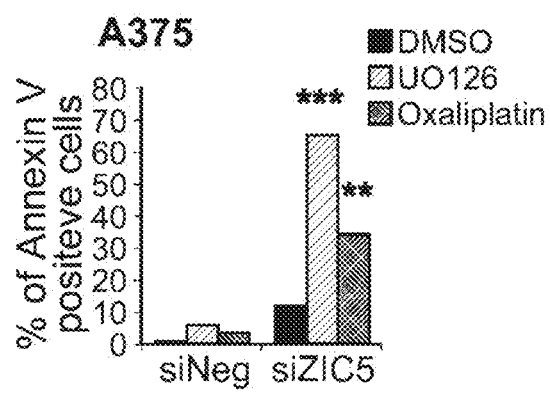
FIG. 36 illustrates measurement results of a percentage (%) of Annexin V-positive cells in A375 cells transfected with siNeg or siZIC5, after being treated with an MEK inhibitor, UO126, or after being treated with oxaliplatin or treated with DMSO in Example 7.

In addition, A375 cells were transfected with siNeg or siZIC5 described in Table 2 in the same manner as Example 1, and then treated with DMSO or UO126 (manufactured by Cell Signaling) solution (which was dissolved in DMSO to become 10 µM), or oxaliplatin (manufactured by Sigma Aldrich, St. Louis, Mo.) solution (which was dissolved in DMSO to become 20 µM) for 48 hours. The result of percentage (%) of Annexin V-positive cells (n=3) in each cell after treatment is shown in FIG. 36. The statistical difference was determined by the Tukey's multiple comparisons of means test (**: P<0.01, *: P<0.05). As a result, regarding the suppression of apoptosis by Zic5, the same results were obtained in the cells treated with an MEK inhibitor, UO126 or a platinum-containing drug, oxaliplatin as in a case of PLX4032 treatment.

In addition, after A375 cells were transfected with siNeg or siZIC5 described in Table 1, or siPDGFD or siITGA6 described in Table 8 in the same manner as Example 1, and then treated with DMSO or PLX4032 solution (which was dissolved in DMSO to become 5 µM) for 24 hours, the level of phosphorylated Stat3 (pStat3), total Stat3 (Stat3), and β-actin in the cells was assessed by western blotting. As a result, regardless of whether PLX4032 treatment was performed or not, phosphorylation of Stat3 was suppressed by ZIC5 or ITGA6 knockdown, but in the cells in which PDGFD knockdown occurred, phosphorylation of Stat3 was suppressed only in a case where PLX4032 treatment was performed (not shown).

When the stably Zic5 gene-expressed line and the stably Flag-expressed line produced in Example 6 were treated with DMSO, or a Stat3 inhibitor, WP1066 (manufactured by Santa Cruz, Dallas, Tex.) solution (which was dissolved in DMSO to become 10 µM) for 24 hours, the suppression of apoptosis by Zic5 was completely suppressed by Stat3 inhibitor treatment (not shown).

Based on these results, it is considered that ZIC5 suppresses apoptosis of melanoma cells through activation of Stat3 by the downstream factors, PDGFD and ITGA6, and therefore contributes to drug resistance, and it is expected that the suppression of these molecules will lead to an improvement of therapeutic effects.

Example 8

Next, with respect to Vemurafenib-resistant cell lines generated, a possibility that Zic5 gene, and the downstream factors, PDGFD and ITGA6 become a treatment target was examined.

Figure 37:
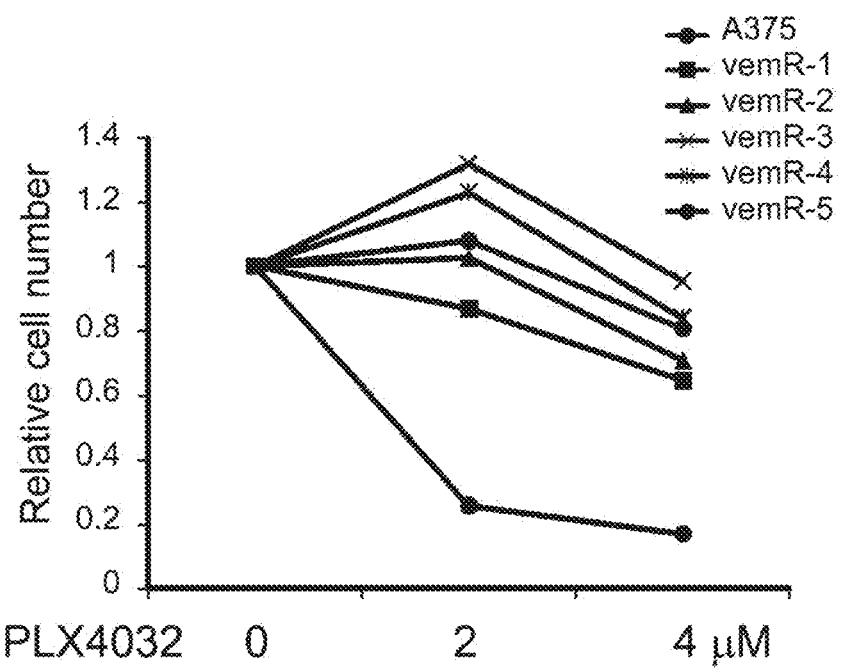
FIG. 37 illustrates measurement results of a relative cell number of 5 Vemurafenib-resistant cell lines (vemR-1 to 5) and A375 cells, after being treated with PLX4032 at each concentration for 48 hours in Example 8.
Figure 38:
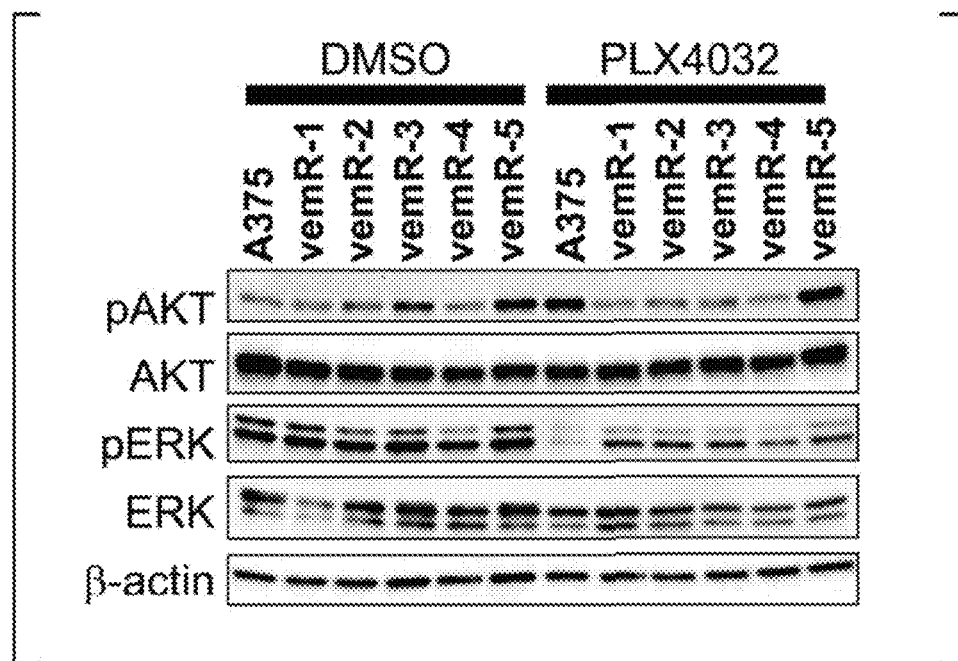
FIG. 38 illustrates western blotting images of vemR-1 to 5 cells and A375 cells after being treated with PLX4032 or after being treated with DMSO of Example 8.
Figure 39:
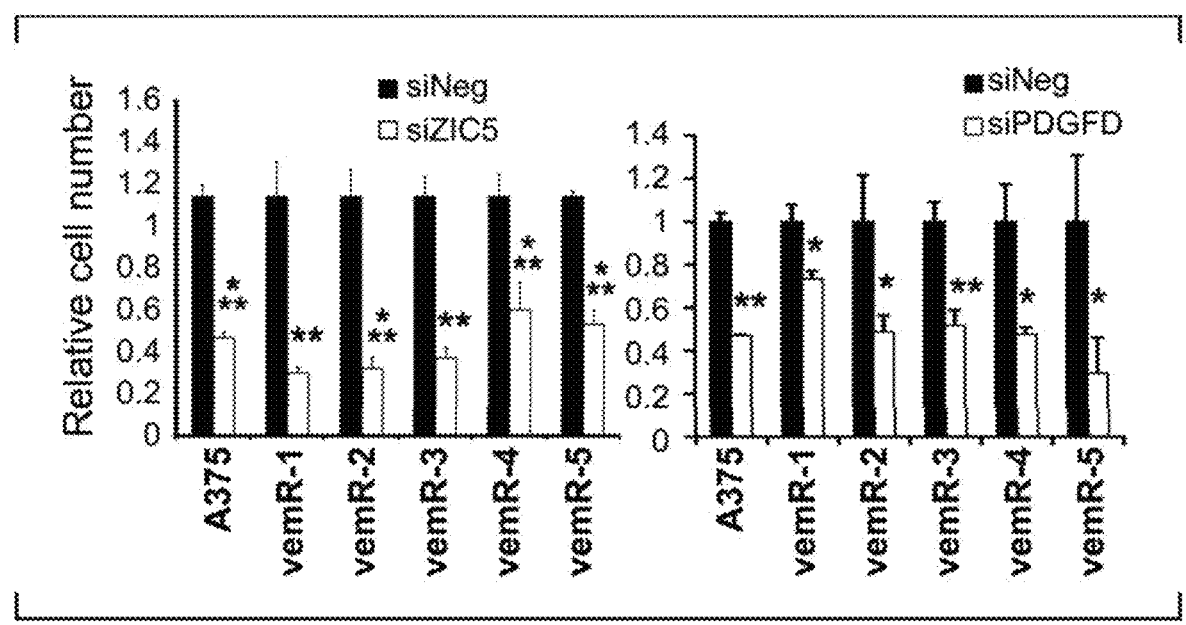
FIG. 39 illustrates measurement results of a relative cell number of vemR-1 to 5 cells and A375 cells transfected with siNeg, siZIC5, or siPDGFD in Example 8.

First, 5 Vemurafenib-resistant cell lines (vemR-1 to 5) were produced using A375 cells. Each cell line was treated with vemurafenib (PLX4032) at 0, 2, or 4 µM for 48 hours, and then the number of cells was counted, and then a relative cell number in which the number of cells with no PLX4032 treatment (PLX4032 concentration is 0 µM) was set to 1 was counted. The result is shown in FIG. 37. It was confirmed that in vemR-1 to 5, a width of decrease in the cells by PLX4032 treatment was smaller than A375 cells, and vemR-1 to 5 had Vemurafenib resistance.

vemR-1 to 5 cells and A375 cells were treated with DMSO or PLX4032 solution (which was dissolved in DMSO to become 5 µM) for 48 hours, and the level of phosphorylated AKT (Ser473) (pAKT), total AKT (AKT), phosphorylated ERK1/2 (Thr202/204) (pERK), total ERK1/2 (ERK), and β-actin of these cells was assessed with western blotting. Western blotting was performed in the same manner as above except that anti-pAKT antibody (manufactured by Cell Signaling), anti-AKT antibody (manufactured by Cell Signaling), anti-pERK antibody (manufactured by Cell Signaling), anti-ERK antibody (manufactured by Cell Signaling), and anti-β-actin antibody (manufactured by Sigma) were used. The result is shown in FIG. 38. As a result, reactivation of ERK was observed in vemR-1 to 5 cells.

vemR-1 to 5 cells and A375 cells were transfected with siNeg or siZIC5 described in Table 1, or siPDGFD described in Table 8 in the same manner as Example 1. The number of cells of each cell 3 days after siRNA transfection was counted, and a relative cell number (n=3) in a case where the number of cells in which A375 cells were transfected with siNeg was set to 1 was calculated. The statistical difference was determined using the Student's t-test (*: P<0.001, : P<0.01, *: P<0.05). The result is shown in FIG. 39. When ZIC5 or PDGFD expression was suppressed by siRNA transfection, the number of cells was reduced and proliferation rate decreased in both cells.

Example 9

Figure 40:
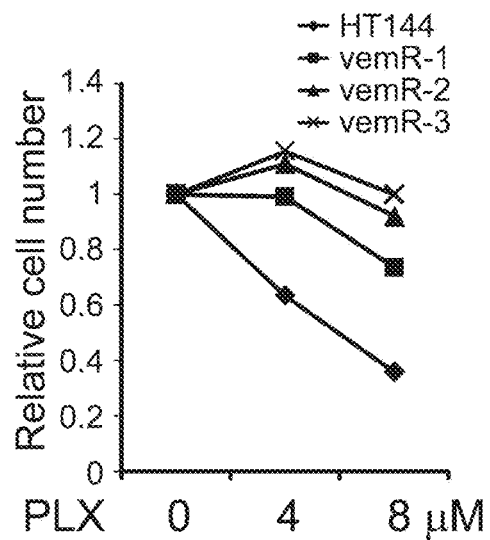
FIG. 40 illustrates measurement results of a relative cell number of 3 Vemurafenib-resistant cell lines (vemR-1 to 3) and HT144 cells, after being treated with PLX4032 at each concentration for 48 hours in Example 9.
Figure 41:
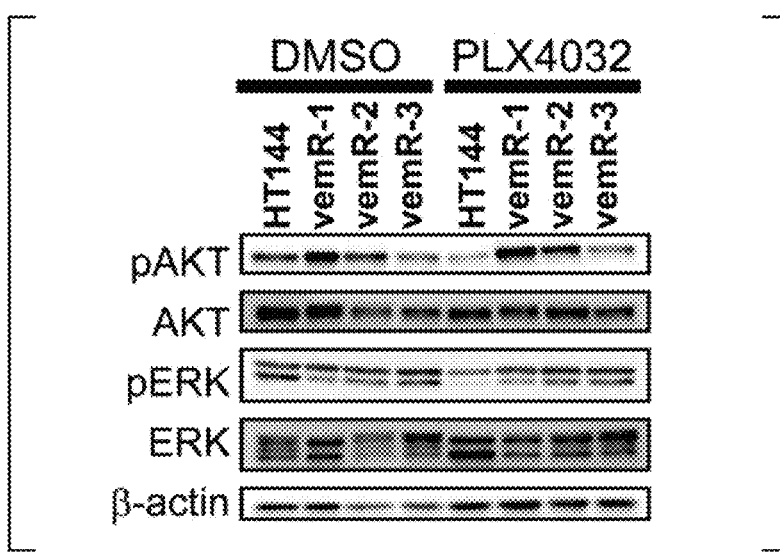
FIG. 41 illustrates western blotting images of vemR-1 to 3 cells and HT144 cells after being treated with PLX4032 or after being treated with DMSO of Example 9.
Figure 42:
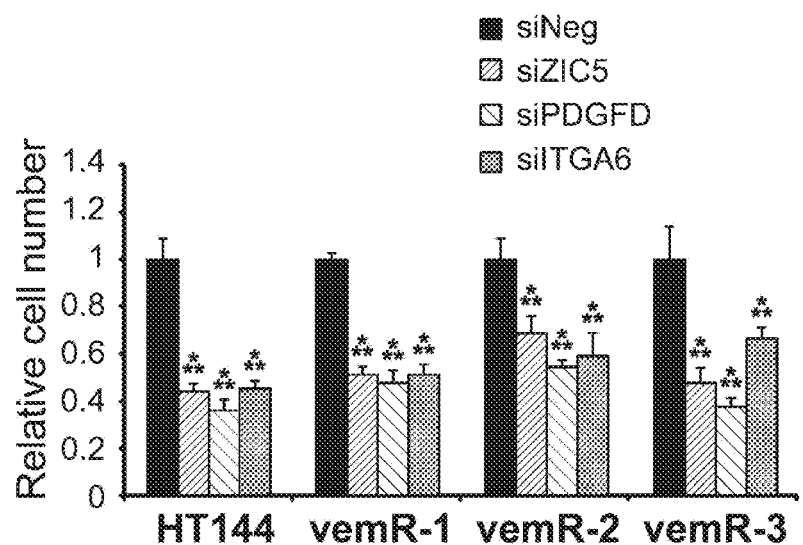
FIG. 42 illustrates measurement results of a relative cell number of vemR-1 to 3 cells and HT144 cells transfected with siNeg, siZIC5, siPDGFD, or siITGA6 in Example 9.

Three Vemurafenib-resistant cell lines (vemR-1 to 3) were produced in the same manner using HT144 cells. Each cell line was treated with vemurafenib (PLX4032) at 0, 4, or 8 µM for 48 hours, and then the number of cells was counted, and then a relative cell number in which the number of cells with no PLX4032 treatment (PLX4032 concentration is 0 µM) was set to 1 was counted. The result is shown in FIG. 40.

vemR-1 to 3 cells and HT144 cells were treated with DMSO or PLX4032 solution (which was dissolved in DMSO to become 5 µM) for 48 hours, and the level of pAKT, AKT, pERK, ERK, and β-actin of these cells was assessed by western blotting in the same manner as Example 8. The result is shown in FIG. 41. As a result, reactivation of both of AKT and ERK was observed in vemR-1 to 3 cells.

vemR-1 to 3 cells and HT144 cells were transfected with siNeg or siZIC5 described in Table 1, or siPDGFD or siITGA6 described in Table 8 in the same manner as Example 1. The number of cells of each cell 3 days after siRNA transfection was counted, and a relative cell number (n=3) in a case where the number of cells in which HT144 cells were transfected with siNeg was set to 1 was calculated. The statistical difference was determined using the Dunnett's multiple comparisons of means test (***: P<0.001). The result is shown in FIG. 42. When ZIC5, PDGFD, or ITGA6 expression was suppressed by siRNA transfection, the number of cells was reduced and proliferation rate decreased in both cells.

Based on the results of Example 8 and Example 9, it was suggested that even with respect to the cells having a resistance to the BRAF inhibitor which was generated in melanoma therapy, Zic5, PDGFD, or ITGA6 knockdown is effective for the therapy.

Example 10

<Zic5 Gene Expression in Human Prostate Cancer>

Figure 43:
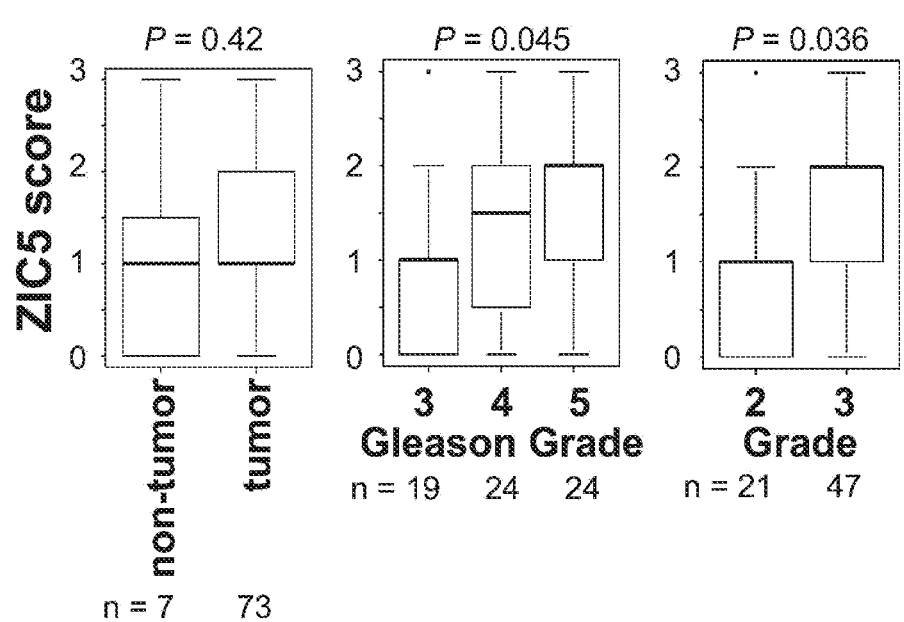
FIG. 43 illustrates results of scoring the expression level of Zic5 gene based on staining intensity of a stained image obtained by immunohistochemically staining a human prostate cancer clinical specimen using anti-ZIC5 antibody in Example 10.

According to database search, it was suggested that Zic5 gene expression was upregulated in metastatic prostate cancer (GDS2546). Therefore, Zic5 gene expression in clinical tissues of human prostate cancer was examined by immunohistochemical staining. Specifically, with respect to 73 tissue sections of human prostate cancer, 7 tissue sections of non-prostate cancer (all purchased from US Biomax), immunohistochemical staining was performed using anti-ZIC5 antibody (manufactured by Aviva systems biology). Stained images of each clinical tissue section by anti-ZIC5 antibody were scored based on staining intensity into 4 stages (0 to 3). In FIG. 43, the scores of noncancerous sections and cancerous sections (left drawing), the scores of sections of grades 3, 4, or 5 according to Gleason's classification (drawing in the middle), and the scores of sections of grades 2 or 3 (right drawing) are shown. The statistical difference was determined using the Mann-Whitney's U-test for the scores of the noncancerous sections and the cancerous sections, and using the Fisher's exact test for the scores of Gleason's classification and Grade. As a result, it was suggested that there was no significant difference in expression between the noncancerous portions and the cancerous portions, but Zic5 gene expression was upregulated in prostate cancer with high-grade.

<Influence of Zic5 Gene Knockdown on Human Prostate Cancer>

The influence of Zic5 knockdown was examined using human prostate cancer cell line, DU145 cells.

Figure 44:
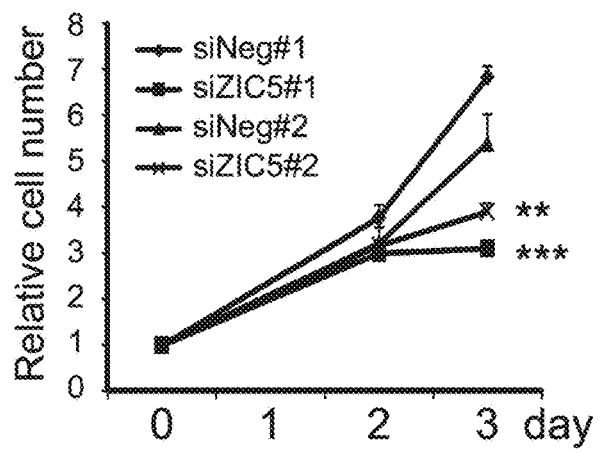
FIG. 44 illustrates measurement results of a relative cell number of DU145 cells transfected with siZIC5#1, siZIC5#2, siNeg#1, or siNeg#2 in Example 10.

First, DU145 cells were transfected with siZIC5#1, siZIC5#2, siNeg#1, or siNeg#2 described in Table 2 in the same manner as Example 1, and the number of cells 0, 2, or 3 days after transfection was counted. The result of calculating a relative cell number of each cell (the number of cells on $0^{th}$ day after transfection (before transfection) was set to 1) (n=3) is shown in FIG. 44. The statistical difference was determined by the Tukey's multiple comparisons of means test (*: $P<0.001$, : $P<0.01$, *: $P<0.05$). As a result, it was revealed that in DU145 cells, cell proliferation rate was decreased by Zic5 gene knockdown by siRNA transfection.

Figure 45:
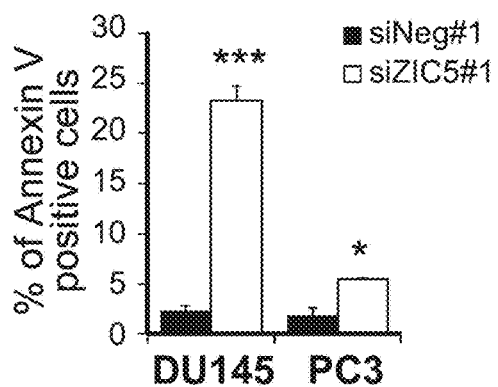
FIG. 45 illustrates measurement results of a percentage (%) of Annexin V-positive cells in DU145 cells or PC cells transfected with siZIC5#1 or siNeg#1 in Example 10.

DU145 cells or PC cells were transfected with siZIC5#1 or siNeg#1 described in Table 2 in the same manner as Example 1. The transfected cells were stained by using FITC labeled Annexin V (manufactured by MBL, Nagoya, Japan) in the same manner as Example 7, and percentage (%) of Annexin V-positive cells (n=3) in each cell was calculated. The statistical difference was determined using the Student's t-test (*: $P<0.001$, : $P<0.01$, *: $P<0.05$). The result is shown in FIG. 45. As a result, it was revealed that in the cells transfected with siZIC5#1, the percentage of Annexin V-positive cells was increased, and that apoptosis was induced by Zic5 gene knockdown.

Figure 46:
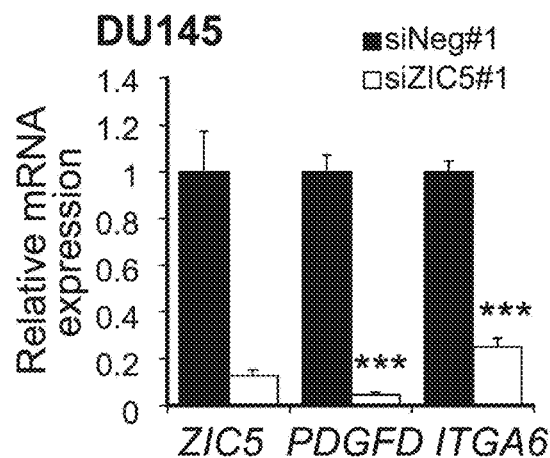
FIG. 46 illustrates measurement results of a relative mRNA expression level of Zic5 gene, PDGFD gene, and ITGA6 gene in DU145 cells transfected with siZIC5#1 or siNeg#1 in Example 10.

DU145 cells were transfected with siZIC5#1 or siNeg#1 described in Table 2 in the same manner as Example 1, and an mRNA expression level of Zic5 gene, PDGFD gene, and ITGA6 gene in each cell after transfection was assessed by qRT-PCR in the same manner as Example 6. The mRNA expression level of Zic5 gene and the like in each cell was normalized to an mRNA expression level of ACTB (β-actin) gene. The result of calculating a relative mRNA expression level of each gene (expression level of the cells transfected with siNeg#1 was set to 1) (n=3) is shown in FIG. 46. The statistical difference was determined using the Student's t-test (*: $P<0.001$, : $P<0.01$, *: $P<0.05$). As a result, the expression of PDGFD gene and ITGA6 gene was significantly reduced by Zic5 gene knockdown.

Figure 47:
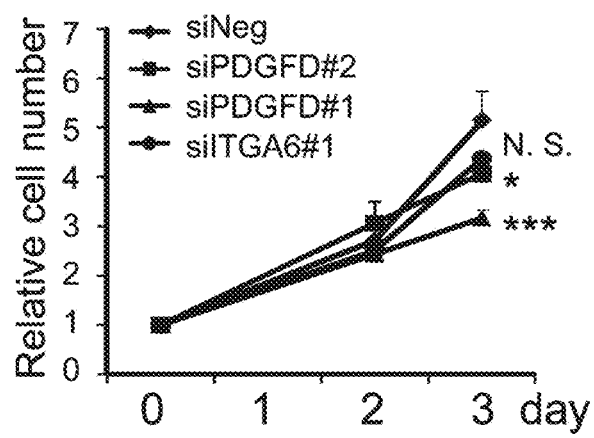
FIG. 47 illustrates measurement results of a relative cell number of DU145 cells transfected with siPDGFD#1, siPDGFD#2, or siITGA6#1 in Example 10.

DU145 cells were transfected with siPDGFD#1, siPDGFD#2, or siITGA6#1 described in Table 8 in the same manner as Example 1, and the number of cells 0, 2, or 3 days after transfection was counted. The result of calculating a relative cell number of each cell (the number of cells on $0^{th}$ day after transfection (before transfection) was set to 1) (n=3) is shown in FIG. 47. The statistical difference was determined by the Tukey's multiple comparisons of means test (*: $P<0.001$, : $P<0.01$, *: $P<0.05$). As a result, cell proliferation rate of DU145 cells was decreased by PDGFD gene knockdown by siRNA transfection, but was hardly affected by ITGA6 gene knockdown.

Figure 48:
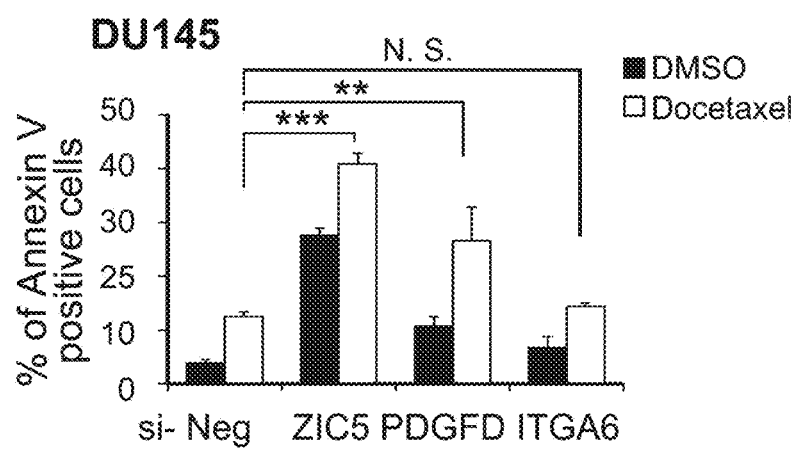
FIG. 48 illustrates measurement results of a percentage (%) of Annexin V-positive cells in DU145 cells which are transfected with siPDGFD#1, siPDGFD#2, or siITGA6#1, and then treated with docetaxel or treated with DMSO in Example 10.

Furthermore, DU145 cells were transfected with siPDGFD#1, siPDGFD#2, or siITGA6#1 described in Table 8 in the same manner as Example 1, and then treated with DMSO, or docetaxel (manufactured by Sigma-Aldrich Co. LLC.) solution (which was dissolved in DMSO to become 5 nM) for 24 hours. The result of percentage (%) of Annexin V-positive cells (n=3) in each cell after treatment is shown in FIG. 48. The statistical difference was determined by the Tukey's multiple comparisons of means test (*: $P<0.001$, : $P<0.01$, *: $P<0.05$). As a result, it was observed that apoptosis induced by docetaxel was significantly increased by Zic5 and PDGFD knockdown, but was hardly affected by ITGA6 knockdown.

Based on these results, it was revealed that in prostate cancer cells, knockdown of PDGFD gene and ITGA6 gene occurred in the downstream of Zic5 gene, cell proliferation rate was decreased by PDGFD gene knockdown, and induction of apoptosis by Docetaxel was enhanced by knockdown of Zic5 gene and PDGFD gene. Based on the above findings, it was suggested that knockdown of Zic5 gene and PDGFD gene is effective for prostate cancer therapy.

Example 11

The influence of PDHFD gene expression and activation of FAK, STAT3, and the like, which are downstream signaling factors thereof, on Zic5 gene expression was examined.

<Influence of PDGFD Gene Knockdown on Zic5 Gene>

A375 cells were transfected with siNeg described in Table 1 and siPDGFD described in Table 8 in the same manner as Example 1, and RNA interference was performed. The expression level of PDGFD gene and Zic5 gene in the obtained cells was measured by western blotting using GAPDH as an internal control. Western blotting was performed according to a method of Kanemaru et al. (refer to NPL 13) using anti-ZIC5 antibody (manufactured by Aviva systems biology), anti-PDGFD antibody (manufactured by Santa Cruz), and anti-GAPDH antibody (manufactured by Cell Signaling).

Figure 49:
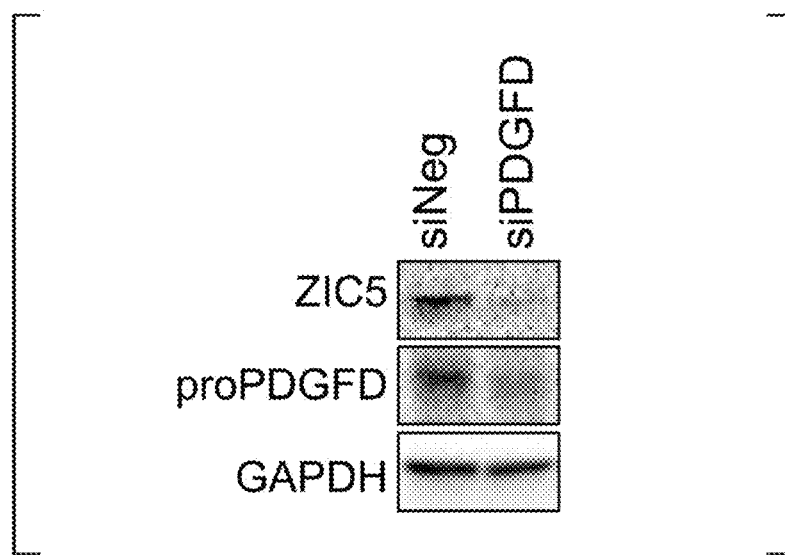
FIG. 49 illustrates western blotting images of A375 cells transfected with siPDGFD or siNeg of Example 11.

A band stained by each antibody is shown in FIG. 49. The top ("ZIC5") is a band stained by anti-ZIC5 antibody, the middle ("pro-PDGFD") is a band stained by anti-PDGFD antibody, and the bottom ("GAPDH") is a band stained by anti-GAPDH antibody. In the cells in which pro-PDGFD knockdown occurred by siPDGFD transfection, ZIC5 knockdown also occurred.

<Influence of PDGFD Gene Overexpression on Zic5 Gene>

With respect to an hPDGFD-overexpressed line which is transfected with hPDGFD expression vector in which cDNA of human PDGFD gene was inserted to plasmid pcDNA, and is selected by G418 treatment, and a pcDNA line (negative control) which is transfected with pcDNA, an empty vector, and is selected by G418 treatment, western blotting was performed to assess the level of phosphorylated FAK (pFAK), phosphorylated STAT3 (pSTAT3), total STAT3 (STAT3), ZIC5, pro-PDGFD, and β-actin. Western blotting was performed in the same manner as above except that anti-pFAK antibody (manufactured by Signalway Antibody), anti-pSTAT3 antibody (manufactured by Cell Signaling), STAT3 antibody (manufactured by BD Biosciences), anti-ZIC5 antibody (manufactured by Aviva systems biology), anti-PDGFD antibody (manufactured by Santa Cruz), and anti-β-actin antibody (manufactured by Sigma) were used.

Figure 50:
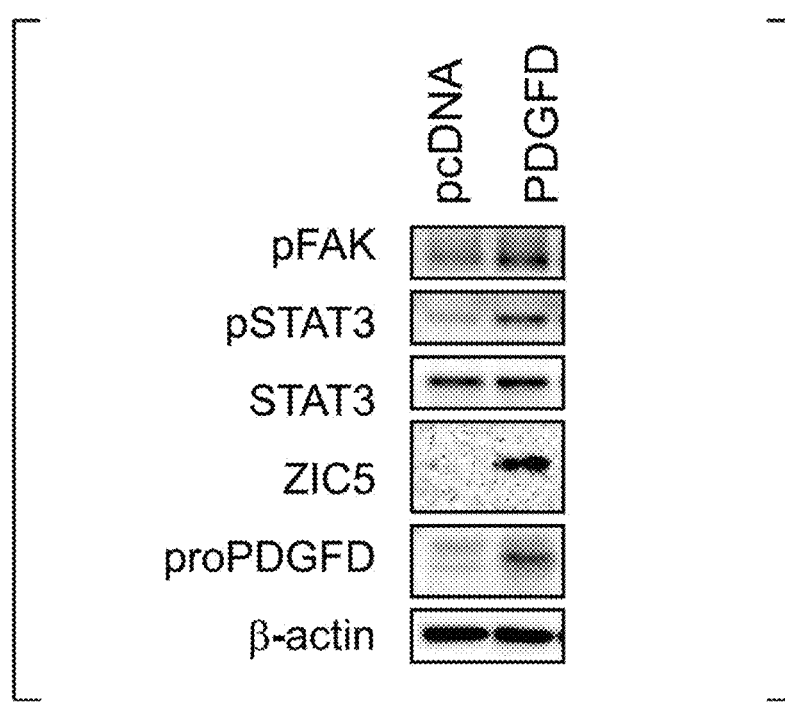
FIG. 50 illustrates western blotting images of hPDGFD-overexpressed lines and pcDNA lines of Example 11.

A band stained by each antibody is shown in FIG. 50. As a result, it was revealed that in the hPDGFD-overexpressed line, ZIC5 expression was greatly upregulated as well as pro-PDGFD.

<Influence of FAK Inhibitor Treatment on Zic5 Gene>

A375 cells were treated in a medium in which a concentration of a FAK inhibitor I (manufactured by Calbiochem) was 0, 1, 2.5, or 5 µM for 24 hours, and the level of ZIC5, pro-PDGFD, pERK, and β-actin was measured by western blotting. Western blotting was performed in the same manner as above except that anti-ZIC5 antibody (manufactured by Aviva systems biology), anti-PDGFD antibody (manufactured by Santa Cruz), anti-pERK antibody (manufactured by Cell Signaling), and anti-β-actin antibody (manufactured by Sigma) were used.

Figure 51:
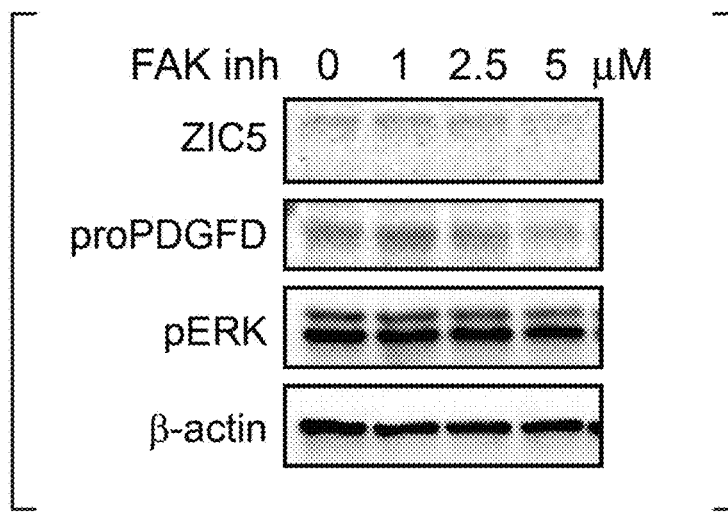
FIG. 51 illustrates western blotting images of A375 cells after FAK inhibitor treatment of Example 11.

A band stained by each antibody is shown in FIG. 51. As a result, it was confirmed that the level of pERK was not changed by the FAK inhibitor treatment, but the expression level of ZIC5 and pro-PDGFD was decreased in accordance with a concentration of the FAK inhibitor.

<Influence of Stat3 Inhibitor Treatment on Zic5 Gene>

A375 cells were treated in a medium in which a concentration of the Stat3 inhibitor, WP1066 (manufactured by Santa Cruz, Dallas, Tex.) was 0, 1, 1.5, 2, 2.5, 3, or 4 µM for 24 hours, and then western blotting was performed to assess the level of ZIC5, pro-PDGFD, pSTAT3, STAT3, and GAPDH. Western blotting was performed in the same manner as above except that anti-ZIC5 antibody (manufactured by Aviva systems biology), anti-PDGFD antibody (manufactured by Santa Cruz), anti-pSTAT3 antibody (manufactured by Cell Signaling), STAT3 antibody (manufactured by BD Biosciences), and anti-GAPDH antibody (manufactured by Cell Signaling) were used.

Figure 52:
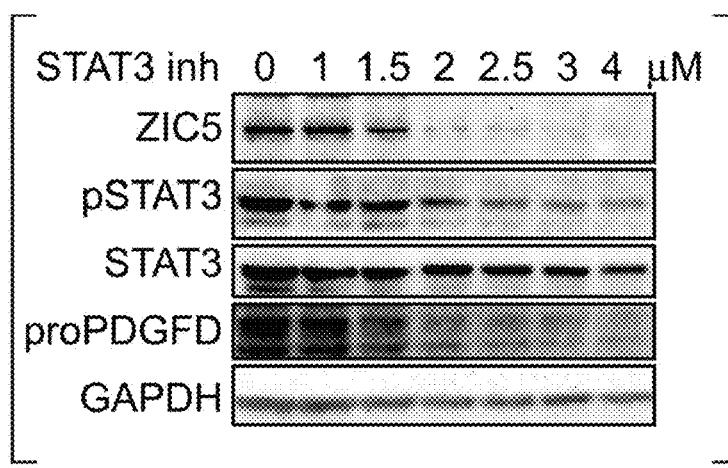
FIG. 52 illustrates western blotting images of A375 cells after STAT3 inhibitor treatment of Example 11.

A band stained by each antibody is shown in FIG. 52. As a result, it was confirmed that the level of STAT3 was not changed by the Stat3 inhibitor treatment, but the expression level of pSTAT3 was decreased in accordance with a concentration of the Stat3 inhibitor. Furthermore, the expression level of pro-PDGFD and the expression level of ZIC5 were decreased in accordance with a concentration of the Stat3 inhibitor, similarly to pSTAT3.

<Influence of IL-6 Treatment on Zic5 Gene>

A375 cells were treated in a medium in which a concentration of Interleukin-6 (IL-6) (manufactured by Novus Biologicals) was 0, 10, or 20 ng/mL for 24 hours, and then western blotting was performed to assess the level of ZIC5, pro-PDGFD, pSTAT3, STAT3, and GAPDH. Western blotting was performed in the same manner as above except that anti-ZIC5 antibody (manufactured by Aviva systems biology), anti-pERK antibody (manufactured by Cell Signaling), anti-pSTAT3 antibody (manufactured by Cell Signaling), STAT3 antibody (manufactured by BD Biosciences), and anti-GAPDH antibody (manufactured by Cell Signaling) were used.

Figure 53:
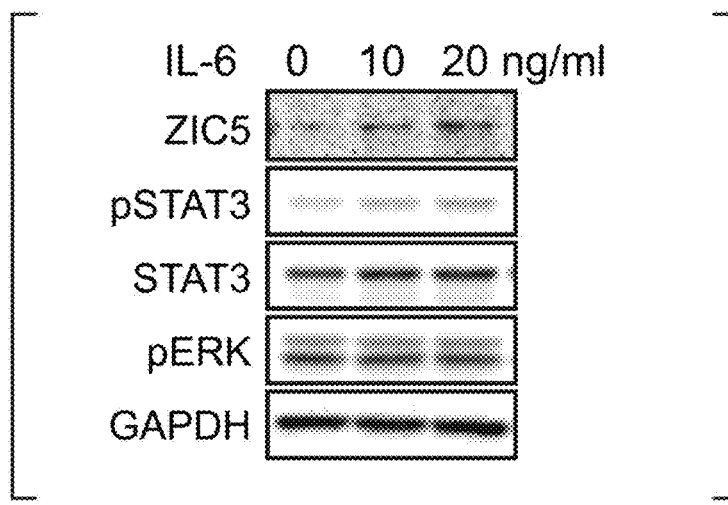
FIG. 53 illustrates western blotting images of A375 cells after IL-6 treatment of Example 11.

A band stained by each antibody is shown in FIG. 53. As a result, it was confirmed that the level of STAT3 and the level of pERK were not changed by the IL-6 treatment, but the expression level of pSTAT3 was increased in accordance with a concentration of the IL-6. Furthermore, the expression level of ZIC5 was increased in accordance with a concentration of the IL-6, similarly to pSTAT3.

Based on these results, it was suggested that signals of PDGFD, FAK, and STAT3, which are regulated to be positive by ZIC5, regulate ZIC5 expression to be positive, and these factors form a positive feedback loop.

Example 12

The influence of Vemurafenib-resistant cell line (vemR-3 cells) produced in Example 8 on knockdown of ZIC5 and PDGFD was examined.

Figure 54:
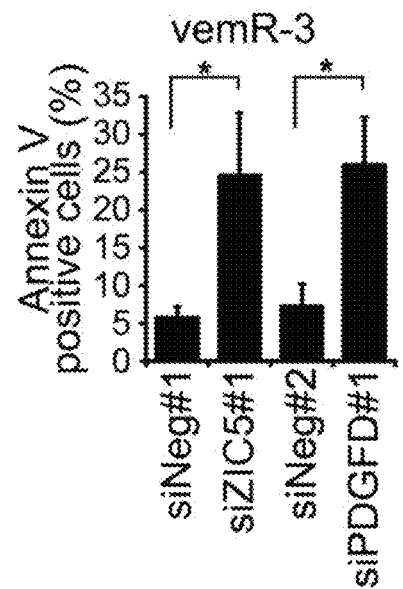
FIG. 54 illustrates measurement results of a percentage (%) of Annexin V-positive cells in vemR-3 cells transfected with siNeg#1, siNeg#2, siZIC5#1, or siPDGFD#1 in Example 12.

<Influence of Knockdown of ZIC5 and PDGFD on Apoptosis> vemR-3 cells were transfected with siNeg#1 or siNeg#2 described in Table 1, siZIC5#1 described in Table 2, or siPDGFD#1 described in Table 8 in the same manner as Example 1 to perform RNA interference. A percentage of apoptotic cells in the obtained cells was detected by using FITC labeled Annexin V (manufactured by MBL, Nagoya, Japan) in the same manner as Example 7. The result of percentage (%) of Annexin V-positive cells (n=3) in each cell is shown in FIG. 54. As a result, it was found that the percentage of Annexin V-positive cells was significantly increased in both of the cells transfected with siZIC5#1 and the cells transfected with siPDGFD#1, and that in the vemR-3 cells, apoptosis was induced by ZIC5 knockdown or PDGFD knockdown.

<Influence of Knockdown of ZIC5 and PDGFD on ERK Activation> vemR-3 cells were transfected with siNeg#1 or siNeg#2 described in Table 1, siZIC5#1 described in Table 2, or siPDGFD#1 described in Table 8, in the same manner as Example 1 to perform RNA interference. The obtained cells were treated with the BRAF inhibitor, PLX4032 or treated with DMSO, and then the level of pERK was accessed by western blotting in the same manner as Example 7. Western blotting was performed according to a method of Kanemaru et al. (refer to NFL 13) using anti-ZIC5 antibody (manufactured by Aviva systems biology), anti-PDGFD antibody (manufactured by Santa Cruz), anti-pERK antibody (manufactured by Cell Signaling), anti-ERK antibody (manufactured by Cell Signaling), and anti-GAPDH antibody (manufactured by Cell Signaling).

Figure 55:
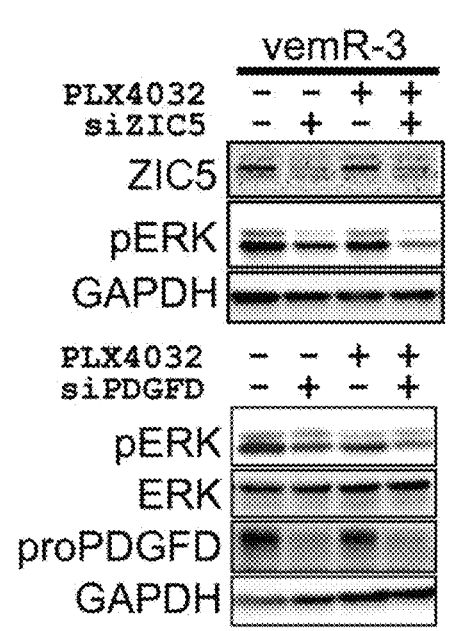
FIG. 55 illustrates western blotting images of vemR-3 cells which are transfected with siZIC5#1 or siPDGFD#1, and then treated with the BRAF inhibitor, PLX4032 of Example 12.

A band stained by antibody is shown in FIG. 55. In the drawing, in "PLX4032 treatment", "+" shows the result of the cells treated with PLX4032, and "−" shows the result of the cells treated with DMSO. In addition, in "siZIC5", "+" shows the result of the cells transfected with siZIC5#1, and "−" shows the result of the cells transfected with siNeg#1. In "siPDGFD", "+" shows the result of the cells transfected with siPDGFD#1, and "−" shows the result of the cells transfected with siNeg#2. In vemR-3 cells, inactivation of ERK (decrease in pERK level) by PLX4032 treatment was not induced, but when ZIC5 knockdown occurred or PDGFD knockdown occurred, the pERK level decreased.

Based on these results, it was considered that a positive feedback signal formed by ZIC5/PDGFD contributes to mutation activation of MEK/ERK signals in the Vemurafenib-resistant cell lines.

The invention claimed is:

1. A method of suppressing tumor cell malignant transformation, the method comprising:
   suppressing or inhibiting a Zic5 gene function to suppress or inhibit acquisition of metastatic ability or acquisition of apoptosis resistance of a tumor cell, wherein the tumor cell is a melanoma cell or a prostate cancer cell.

2. The method of suppressing tumor cell malignant transformation according to claim 1,
   wherein suppressing or inhibiting the Zic5 gene function is carried out by inhibiting expression of the Zic5 gene by RNA interference.

3. A method of treating melanoma, comprising administering an effective amount of an anti-tumor agent to a subject in need thereof,
   wherein the anti-tumor agent comprises a substance that suppresses or inhibits a Zic5 gene function as an active ingredient.

4. The method according to claim 3,
   wherein the melanoma is resistant to a BRAF inhibitor, or the melanoma has no sensitivity to BRAF inhibitor treatment.

5. A method of treating prostate cancer, comprising administering an effective amount of an anti-tumor agent to a subject in need thereof, wherein the anti-tumor agent comprises a substance that suppresses or inhibits a Zic5 gene function as an active ingredient.

6. The method according to claim 5, wherein the substance suppresses or inhibits the Zic5 gene function by inhibiting expression of the Zic5 gene by RNA interference.

7. The method of suppressing tumor cell malignant transformation according to claim 1, wherein suppressing or inhibiting the Zic5 gene function is carried out by a substance inhibiting an interaction between a Zic5 protein and a promoter sequence of a gene that codes for E-cadherin, a substance inhibiting Zic5 protein subnuclear localization, or a substance degrading the Zic5 protein.

8. The method of suppressing tumor cell malignant transformation according to claim 1, wherein the tumor cell is resistant to a BRAF inhibitor.

9. The method according to claim 3, wherein the substance suppresses or inhibits the Zic5 gene function by inhibiting expression of the Zic5 gene by RNA interference.

10. The method according to claim 1, wherein the suppressing or inhibiting a Zic5 gene function comprises providing at least one selected from the group consisting of small interfering RNA that comprises a partial region of cDNA of Zic5 gene, a short hairpin RNA that comprises a partial region of cDNA of Zic5 gene, miRNA that comprises a partial region of cDNA of Zic5 gene, and an anti-ZIC5 antibody.

11. The method according to claim 3, wherein the anti-tumor agent at least one selected from the group consisting of small interfering RNA that comprises a partial region 4 of cDNA of Zic5 gene, a short hairpin RNA that comprises a partial region of cDNA of Zic5 gene, miRNA that comprises a partial region of cDNA of Zic5 gene, and an anti-ZIC5 antibody.

12. The method according to claim 5, wherein the anti-tumor agent at least one selected from the group consisting of small interfering RNA that comprises a partial region of cDNA of Zic5 gene, a short hairpin RNA that comprises a partial region of cDNA of Zic5 gene, miRNA that comprises a partial region of cDNA of Zic5 gene, and an anti-ZIC5 antibody.

* * * * *

SEQUENCE LISTING

<160> NUMBER OF SEQ ID NOS: 36

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: CDH1
      (E-cadherin) forward primer

<400> SEQUENCE: 1
ggactttggc gtgggccagg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: CDH1
      (E-cadherin) reverse primer

<400> SEQUENCE: 2
ccctgtccag ctcagcccga                                                    20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: GAPDH
      forward primer

<400> SEQUENCE: 3
agcctcccgc ttcgctctct                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: GAPDH
      reverse primer

<400> SEQUENCE: 4
ccaggcgccc aatacgacca                                                    20

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: siZic5 #1

<400> SEQUENCE: 5
aagattcgag gctgtgacaa a                                                  21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: siZic5 #2

<400> SEQUENCE: 6
ggctgtgaca aatcctaca                                                     19

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: siNeg #1

<400> SEQUENCE: 7
aattctccga acgtgtcacg t                                              21

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: siNeg #2

<400> SEQUENCE: 8
atccgcgcga tagtacgta                                                 19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: ZIC5
      forward primer

<400> SEQUENCE: 9
caccagtgac aagccctact                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: ZIC5
      reverse primer

<400> SEQUENCE: 10
gagtaaccaa ggggtcctgg                                                20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: shZic5-1

<400> SEQUENCE: 11
ggctgtgaca aatcctaca                                                 19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: shZic5-2

<400> SEQUENCE: 12
gattcgaggc tgtgacaaa                                                 19

<210> SEQ ID NO 13
<211> LENGTH: 30
<212> TYPE: DNA
<213> ORGANISM: Artificial Sequence
<220> FEATURE:

<223> OTHER INFORMATION: Description of Artificial Sequence: ZIC5-ZF
forward primer

<400> SEQUENCE: 13
cccggatccg tgaatcacgt cacggtggag                                    30

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: ZIC5-ZF
reverse primer

<400> SEQUENCE: 14
cccctcgagt tagcagtgaa tcttcatgtg cttcc                              35

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: GBS

<400> SEQUENCE: 15
gatcctgtga ttttcgtctt gggtggtctc cctcg                              35

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: M5

<400> SEQUENCE: 16
gatcctgtga ttttcgtctt gggtgatctc cctcg                              35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: pCDH1

<400> SEQUENCE: 17
tcagccaatc agcggtacgg ggggcggtgc ctccg                              35

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: ZIC5-ZF
forward primer

<400> SEQUENCE: 18
tagagggtca ccgcgtctat                                               20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: ZIC5-ZF
reverse primer

<400> SEQUENCE: 19

```
attggctgag ggttcacctg                                              20
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Negative
      control forward primer

<400> SEQUENCE: 20

```
gcagtgggat aggagcagac                                              20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Negative
      control reverse primer

<400> SEQUENCE: 21

```
ccgtggctac tggatgtgtc                                              20
```

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: pCDH1
      forward primer

<400> SEQUENCE: 22

```
cacactcgag caccactgca ctccagcttg g                                 31
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: pCDH1
      reverse primer

<400> SEQUENCE: 23

```
ctccaagggc ccatggctgg                                              20
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: M5mut
      forward primer

<400> SEQUENCE: 24

```
ctccggggct cacctggct                                               19
```

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: M5mut
      reverse primer

<400> SEQUENCE: 25

```
gcatcaccccc ccgtaccgct gattggctga g          31
```

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: GBSmut
      forward primer

<400> SEQUENCE: 26

```
ctccggggct cacctggct                          19
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: GBSmut
      reverse primer

<400> SEQUENCE: 27

```
gcaccacccc ccgtaccgct gattggctga g            31
```

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: siPDGFD #1

<400> SEQUENCE: 28

```
caggaattac tcggtcaata t                       21
```

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: siPDGFD #2

<400> SEQUENCE: 29

```
aaggtatatc atcaacttct a                       21
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: siITGA6 #1

<400> SEQUENCE: 30

```
cacgcggatc gagtttgata a                       21
```

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: ACTB
      (beta-Actin) forward primer

<400> SEQUENCE: 31

```
gccctggcac ccagcacaat                         20
```

<210> SEQ ID NO 32

```
<211> LENGTH: 20
<212> TYPE: DNA
<213> ORGANISM: Artificial Sequence
<220> FEATURE:
<223> OTHER INFORMATION: Description of Artificial Sequence: ACTB
      (beta-Actin) reverse primer

<400> SEQUENCE: 32
ggaggggccg gactcgtcat                                          20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: PDGFD
      forward primer

<400> SEQUENCE: 33
aagatttcca acccgcagca                                          20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: PDGFD
      reverse primer

<400> SEQUENCE: 34
tccagagcat ccgcaatcag                                          20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: ITGA6
      forward primer

<400> SEQUENCE: 35
gagccgtggt tttgctgaag                                          20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: ITGA6
      reverse primer

<400> SEQUENCE: 36
tgccacccat ccttgttgag                                          20
```